United States Patent
Eloit et al.

(10) Patent No.: US 11,542,563 B2
(45) Date of Patent: Jan. 3, 2023

(54) METHOD FOR DISCRIMINATING BETWEEN LIVE AND DEAD MICROBES IN A SAMPLE

(71) Applicant: PATHOQUEST, Paris (FR)

(72) Inventors: Marc Eloit, Paris (FR); Pascale Beurdeley, Fontenay-sous-bois (FR); Stéphane Cruveiller, Yerres (FR)

(73) Assignee: PATHOQUEST, Paris (FR)

( * ) Notice: Subject to any disclaimer, the term of this patent is extended or adjusted under 35 U.S.C. 154(b) by 0 days.

(21) Appl. No.: 17/075,012

(22) Filed: Oct. 20, 2020

(65) Prior Publication Data

US 2021/0087642 A1    Mar. 25, 2021

Related U.S. Application Data

(63) Continuation of application No. PCT/EP2019/066374, filed on Jun. 20, 2019.

(30) Foreign Application Priority Data

Jun. 20, 2018  (EP) ..................... 18305777
Apr. 3, 2019  (EP) ..................... 19305439

(51) Int. Cl.
*C12Q 1/68* (2018.01)
*C12Q 1/70* (2006.01)
*C12Q 1/6806* (2018.01)
*C12Q 1/6869* (2018.01)
*C12Q 1/6888* (2018.01)

(52) U.S. Cl.
CPC ............. *C12Q 1/70* (2013.01); *C12Q 1/6806* (2013.01); *C12Q 1/6869* (2013.01); *C12Q 1/6888* (2013.01); *C12Q 2535/101* (2013.01); *C12Q 2535/122* (2013.01); *C12Q 2563/179* (2013.01)

(58) Field of Classification Search
CPC ....................................................... C12Q 1/68
See application file for complete search history.

(56) References Cited

U.S. PATENT DOCUMENTS

2009/0104162 A1*  4/2009  Kim .................. A61K 35/28
                                                          424/93.7
2019/0177785 A1*  6/2019  Ameres ................ C12Q 1/6869

FOREIGN PATENT DOCUMENTS

WO    2004101825 A1   11/2004
WO    2019242991 A1   12/2019

OTHER PUBLICATIONS

Riggio et al., Molecular detection of transcriptionally active bacteria from failed prosthetic hip joints removed during revision arthroplasty, Eur J Clin Microbiol Infect Dis. Jul. 2010;29(7):823-34. doi: 10.1007/s10096-010-0934-y. Epub 2010.*

(Continued)

*Primary Examiner* — Aaron A Priest
(74) *Attorney, Agent, or Firm* — Maier & Maier, PLLC

(57) ABSTRACT

A method for discriminating between live and dead microbes in a sample, by discriminating between transcriptionally-active and inert microbial nucleic acid sequences in the sample. In particular, the method is based on the comparison of levels of nucleotide substitution in a sample cultured in presence of an RNA-labelling agent. Also, a diagnosis method of microbial infections in a subject; and methods of assessing the risk of contamination of a sample, implementing the method for discriminating between live and dead microbes in a sample.

22 Claims, 9 Drawing Sheets

(56) References Cited

OTHER PUBLICATIONS

Ronholm et al., Navigating Microbiological Food Safety in the Era of Whole-Genome Sequencing, Clin Microbiol Rev. Oct. 2016;29(4):837-57. doi: 10.1128/CMR.00056-16.*
University of Oslo Wiki, BLAST for dummies, available at https://wiki.uio.no/mn/ibv/bioinfwiki/index.php/BLAST_for_dummies#Aligning_query_and_hit_sequences, accessed May 24, 2021.*
Metagenomics—E-value & Bit-score, available at https://www.metagenomics.wiki/tools/blast/evalue, published May 30, 2017, accessed Oct. 6, 2021.*
Altschul, S. F., et al. Basic Local Alignment Search Tool. J Mol Biol. Oct. 5, 1990; 215(3):403-10.
Baptista, M. A. P., et al. RNA dynamics revealed by metabolic RNA labeling and biochemical nucleoside conversions. Nat Methods. Feb. 28, 2018; 15(3):171-172.
Belobrov, S., et al. The role of human papillomavirus in p16-positive oral cancers. Journal of Oral Pathology & Medicine. Jan. 2018; 47(1):18-24.
Black, K. A., et al. Abbreviated Pathway for Biosynthesis of 2-Thiouridine in Bacillus subtilis. Journal of Bacteriology. Jun. 2015; 197(11):1952-62.
Chang, S., et al. A Simple and Efficient Method for Isolating RNA from Pine Trees. Plant Molecular Biology Reporter. Jun. 1993. 11(2):113-116.
Chomczynski, P. A Reagent for the Single-Step Simultaneous Isolation of RNA, DNA and Proteins from Cell and Tissue Samples. Biotechniques. Sep. 1993; 15(3):532-4, 536-7.
Cleary, M D., et al. Biosynthetic labeling of RNA with uracil phosphoribosyltransferase allows cell-specific microarray analysis of mRNA synthesis and decay. Nature Biotechnology. Feb. 2005; 23(2):232-7.
Eisenberg, E., et al. Human housekeeping genes, revisited. Trends Genet. Oct. 2013; 29(10):569-74.
Garibaldi, A., et al. Isolation of Newly Transcribed RNA Using the Metabolic Label 4-Thiouridine. Methods Mol Biol. 2017; 1648:169-176.
Herzog, V. A., et al. Thiol-linked alkylation of RNA to assess expression dynamics. Nat Methods. Dec. 2017; 14(12):1198-1204.
Huang, C., et al. Synthesis and Labeling of RNA In Vitro. Curr Protoc Mol Biol. Apr. 2013; Chapter 4: Unit 4.15.
Jiang, H., et al. Skewer: a fast and accurate adapter trimmer for next-generation sequencing paired-end reads. BMC Bioinformatics. Jun. 12, 2014; 15:182.
Jürges, C., et al. Dissecting newly transcribed and old RNA using GRAND-SLAM. Bioinformatics. Jul. 1, 2018; 34(13):i218-i226.
Kambampati, R., et al. MnmA and IscS Are Required for in Vitro 2-Thiouridine Biosynthesis in *Escherichia coli*. Biochemistry. Feb. 4, 2003; 42(4):1109-17.
Kent, W. J., et al. The Human Genome Browser at UCSC. Genome Res. Jun. 2002; 12(6):996-1006.
Kuriz, S., et al. Versatile and open software for comparing large genomes. Genome Biol. 2004; 5(2):R12.
Li, H., et al. Fast and accurate short read alignment with Burrows-Wheeler transform. Bioinformatics. Jul. 15, 2009; 25(14):1754-60.
Li, H. Minimap2: pairwise alignment for nucleotide sequences. Bioinformatics. Sep. 15, 2018; 34(18):3094-3100.
Liu, Y., et al. Specific labeling: An effective tool to explore the RNA world. Bioessays. Feb. 2016; 38(2):192-200.
Ma, H., et al. Chemical Induction of Endogenous Retrovirus Particles from the Vero Cell Line of African Green Monkeys. Journal of Virology. Jul. 2011; 85(13):6579-88.
Manghera, M., et al. The sense behind retroviral anti-sense transcription. Virology Journal. Jan. 14, 2017; 14(1):9.
Marcinowski, L. et al. Real-time Transcriptional Profiling of Cellular and Viral Gene Expression during Lytic Cytomegalovirus Infection. PLoS Pathog. Sep. 2012; 8(9):e1002908.
Matsushima, W., et al. SLAM-ITseq: Sequencing cell type-specific transcriptomes without cell sorting. bioRxiv 235093. Dec. 16, 2017.
Miller, M. R., et al. TU-tagging: cell type-specific RNA isolation from intact complex tissues. Nat Methods. Jun. 2009; 6(6):439-41.
Mose, L. E., et al. ABRA: improved coding indel detection via assembly-based realignment. Bioinformatics. Oct. 2014; 30(19):2813-5.
Mueller, E. G., et al. Identification of a gene involved in the generation of 4-thiouridine in tRNA. Nucleic Acids Res. Jun. 1, 1998; 26(11):2606-10.
Norman, K. L., et al. Modulation of Hepatitis C Virus RNA Abundance and the Isoprenoid Biosynthesis Pathway by MicroRNA miR-122 Involves Distinct Mechanisms. Journal of Virology. Jan. 2010; 84(1):666-70.
Oda, T., et al. Molecular Cloning, Complete Nucleotide Sequence, and Gene Structure of the Provirus Genome of a Retrovirus Produced in a Human Lymphoblastoid Cell Line. Virology. Dec. 1988; 167(2):468-76.
Olson, N. D., et al. Best practices for evaluating single nucleotide variant calling methods for microbial genomics. Frontiers in Genetics. Jul. 7, 2015; 6:235.
Quinlan, A. R., et al. BEDTools: a flexible suite of utilities for comparing genomic features. Bioinformatics. Mar. 15, 2010; 26(6):841-2.
Riggio, M. P., et al. Molecular detection of transcriptionally active bacteria from failed prosthetic hip joints removed during revision arthroplasty. Eur J Clin Microbiol Infect Dis. Jul. 2010; 29(7):823-34.
Riml, C., et al. Osmium-Mediated Transformation of 4-Thiouridine to Cytidine as Key To Study RNA Dynamics by Sequencing. Angew Chem Int Ed Engl. Oct. 16, 2017; 56(43):13479-13483.
Russo, J., et al. Metabolic Labeling and Recovery of Nascent RNA to Accurately Quantify mRNA Stability. Methods. May 1, 2017; 120:39-48.
Sakuma, C., et al. Novel endogenous simian retroviral integrations in Vero cells: implications for quality control of a human vaccine cell substrate. Scientific Reports. Jan. 12, 2018; 8(1):644.
Schofield, J. A., et al. TimeLapse-seq: adding a temporal dimension to RNA sequencing through nucleoside recoding. Nat Methods. Mar. 2018; 15(3):221-225.
Schulz, D., et al. Current Approaches for RNA Labeling in Vitro and in Cells Based on Click Reactions. Chembiochem. Nov. 3, 2014; 15(16):2342-7.
Tani, H., et al. Genome-wide technology for determining RNA stability in mammalian cells: Historical perspective and recent advantages based on modified nucleotide labeling RNA Biology. Oct. 2012; 9(10):1233-8.
Wallner, G., et al. Characterization and complete genome sequences of high- and low-virulence variants of tick-borne encephalitis virus. Journal of General Virology. May 1996; 77 ( Pt 5):1035-42.

* cited by examiner

METHOD FOR DISCRIMINATING BETWEEN LIVE AND DEAD MICROBES IN A SAMPLE

FIELD

The present invention relates to a method for discriminating between live and dead microbes in a sample, by discriminating between transcriptionally-active and inert microbial nucleic acid sequences in the sample. In particular, the method according to the present invention is based on the comparison of levels of nucleotide substitution in a sample cultured in presence of an RNA-labelling agent.

The present invention further relates to a diagnosis method of microbial infections in a subject; and to methods of assessing the risk of contamination of a sample, implementing the method for discriminating according to the present invention.

BACKGROUND

The ability to detect viruses in cells, and more generally, microbes, has numerous applications in the field of diagnosis, where it proves useful in the identification of infectious agents leading, e.g., to diseases; in biomedical research, where it conditions the interpretation of experimental results; or in the safety evaluation of potentially contaminated samples; or the viability of microorganisms used in biotechnological process.

Beyond the now standard technique of detection relying on the amplification of microorganism-specific nucleic acid sequences, several techniques have emerged to circumvent the major limitation of techniques based solely on amplification, which is the inability to distinguish between dead microorganisms from active (or replicative) microorganisms, including latent viruses. In the context of screening a biological sample, the ability to establish this distinction is crucial as the presence of an active microbial agent may have consequences different from those associated with the presence of dead and/or inactive microbes, in particular viruses.

These techniques can be based on the detection of sequences specific to the replicating viruses: the presence of RNAs in the case of DNA viruses, the stoichiometry of positive-relative to negative-sense RNAs in the case of negative-sense single-stranded RNA viruses, the presence of negative-sense RNAs (antigenome) in the case of positive-sense single-stranded RNA viruses and the presence of DNA and positive-sense spliced RNA in the case of retroviruses. These techniques are based on the amplification of reverse-complement strand such as, e.g., RT-PCR, or on RNA sequencing (RNA-seq, also called whole transcriptome shotgun sequencing) with high-throughput sequencing methods, particularly stranded RNA-seq techniques.

The current techniques still have several limitations: first and foremost, the current techniques do not permit the distinction between contaminating RNAs, such as replication intermediates present independently of the presence of active microbes—such as active viral particles—in the sample, and RNAs associated with the presence of replicating microbes, such as viruses, in the sample. The efficiency of such techniques in the detection of replicating double-stranded RNA viruses still awaits demonstration. In the case of positive-sense single-stranded RNA viruses, the small number of negative-sense RNA species produced hinders sensitivity of the detection technique available. In the case of negative-sense single-stranded RNA viruses, distinction between positive-strand antigenome and specific transcripts is difficult and require a virus species-specific bioinformatics analysis.

Another characteristic of the RNA species associated with the presence of replicating viruses (and more globally, replicating microbes) is that they are, contrary to potential contaminating RNAs, in the process of being synthetized (i.e., in the host cell in the case of viruses; or directly within the bacteria, fungus or else, in the case of other microbes). Several techniques to label and purify nascent transcript (also referred to as RNA metabolic labelling techniques) have been described. For instance, the incorporation of 4-thiouridine (4sU) or other type of uridine analogs (BudR) has been used to purify nascent eukaryotic mRNAs transcripts and/or investigate the dynamics of transcriptional networks (Herzog et al., 2017. *Nat Methods.* 14(12):1198-1204; Tani et al., 2012. *RNA Biol.* 9(10):1233-8).

Here, the Inventors have designed, optimized and validated a method for the detection of virus-infected cells, including by new viral strain/species, relying on the detection of viral RNA synthesis inside the cells of a biological sample using metabolic labelling. The Inventors have further shown herein that this method is also readily implementable to the detection of any transcriptionally-active microbe, when relying on the detection of microbial RNA synthesis in a sample using metabolic labelling. These include, e.g., the detection of viral, bacterial, archaeal, fungal or protozoal infections or contaminations by living microorganisms and differentiation from carryover of dead microorganisms.

SUMMARY

The present invention relates to an in vitro method for discriminating between live and dead microbes in a sample, comprising discriminating between transcriptionally-active and inert microbial nucleic acid sequences in the sample, wherein the method comprises the steps of:

(a) sequencing a first set of RNAs extracted from the sample, wherein the first set of RNAs is obtained by culturing the sample in presence of an RNA-labelling agent and further by submitting the extracted RNAs to conditions allowing for nucleotide substitution; thereby obtaining a first set of sequence reads;

(b) comparing the number of substituted nucleotides in the first set of sequence reads mapping against at least one microbial nucleic acid sequence hit with a control sequence; and (c) concluding that the at least one microbial nucleic acid sequence hit belongs to a live microbe if the number of substituted nucleotides in the sequence reads mapping against said at least one microbial nucleic acid sequence hit in the first set of sequence reads is greater than the number of nucleotides randomly substituted in the control sequence.

In one embodiment, the in vitro method for discriminating between live and dead microbes in a sample comprises discriminating between transcriptionally-active and inert microbial nucleic acid sequences in the sample, wherein the method comprises the steps of:

(a) sequencing a first set of RNAs extracted from the sample, wherein the first set of RNAs is obtained by culturing the sample in presence of an RNA-labelling agent and further by submitting the extracted RNAs to conditions allowing for nucleotide substitution; thereby obtaining a first set of sequence reads;

(b) comparing the number of substituted nucleotides in the first set of sequence reads mapping against at least one microbial nucleic acid sequence hit with a control sequence; and
(c) concluding that the at least one microbial nucleic acid sequence hit belongs to a live microbe if the number of substituted nucleotides in the sequence reads mapping against said at least one microbial nucleic acid sequence hit in the first set of sequence reads is greater than the number of nucleotides randomly substituted in the control sequence, wherein the control sequence is not a second set of sequence reads mapping against said at least one microbial nucleic acid sequence hit, said second set of sequence reads being obtained by sequencing a second set of RNAs obtained by culturing the sample in absence of an RNA-labelling agent.

In one embodiment, the control sequence is selected from:
a second set of sequence reads mapping against said at least one microbial nucleic acid sequence hit, wherein the second set of sequence reads is obtained by sequencing a second set of RNAs obtained by culturing the sample in absence of an RNA-labelling agent;
a second set of sequence reads mapping against said at least one microbial nucleic acid sequence hit, wherein the second set of sequence reads is obtained by sequencing a second set of RNAs obtained by culturing the sample in presence of an RNA-labelling agent but without submitting the extracted RNAs to conditions allowing for nucleotide substitution;
a consensus microbial nucleic acid sequence, obtained from the sequence reads or contigs of the first set of sequence reads mapping against the at least one microbial nucleic acid sequence hit;
a sequence corresponding to the same microbial nucleic acid sequence hit found in the closest microbial strain identified in nucleic acid sequence databases; and/or
an analogous sequence corresponding to the same microbial nucleic acid sequence hit identified in nucleic acid sequence databases.

In one embodiment, the control sequence is selected from:
a second set of sequence reads mapping against said at least one microbial nucleic acid sequence hit, wherein the second set of sequence reads is obtained by sequencing a second set of RNAs obtained by culturing the sample in presence of an RNA-labelling agent but without submitting the extracted RNAs to conditions allowing for nucleotide substitution;
a consensus microbial nucleic acid sequence, obtained from the sequence reads or contigs of the first set of sequence reads mapping against the at least one microbial nucleic acid sequence hit;
a sequence corresponding to the same microbial nucleic acid sequence hit found in the closest microbial strain identified in nucleic acid sequence databases; and/or
an analogous sequence corresponding to the same microbial nucleic acid sequence hit identified in nucleic acid sequence databases.

In one embodiment, the in vitro method of the invention comprises:
(a) sequencing a first and a second set of RNAs extracted from the sample, wherein the first and the second set of RNAs are obtained by culturing the sample in presence of an RNA-labelling agent, thereby obtaining labelled RNAs, and wherein the first set of RNAs is obtained from a first fraction of the labelled RNAs which is submitted to conditions allowing for nucleotide substitution, and the second set of RNAs is obtained from a second fraction of the labelled RNAs which is not submitted to conditions allowing for nucleotide substitution, thereby obtaining a first and a second set of sequence reads,
(b) comparing the number of substituted nucleotides in the first set of sequence reads mapping against at least one microbial nucleic acid sequence hit with the number of substituted nucleotides in the second set of sequence reads mapping against said at least one microbial nucleic acid sequence hit, and
(c) concluding that the at least one microbial nucleic acid sequence hit belongs to a live microbe if the number of substituted nucleotides in the sequence reads mapping against the at least one microbial nucleic acid sequence hit in the first set of sequence reads is greater than in the second set of sequence reads.

In one embodiment, the in vitro method is for discriminating between infectious and non-infectious viral nucleic acid sequences in a cell sample, and comprises:
(a) sequencing a first and a second set of RNAs extracted from the cell sample, wherein the first set of RNAs is obtained by culturing the cell sample in presence of an RNA-labelling agent and the second set of RNAs is obtained by culturing the cell sample in absence of an RNA-labelling agent, thereby obtaining a first and a second set of sequence reads,
(b) identifying at least one viral nucleic acid sequence hit mapped against at least one sequence read of the first set of sequence reads,
(c) comparing the number of substituted nucleotides in the sequence reads mapping the at least one identified viral nucleic acid sequence hit in the first and second set of sequence reads, and
(d) concluding that the at least one viral nucleic acid sequence hit belongs to an infectious virus if the number of substituted nucleotides in the sequence reads mapping the at least one identified viral nucleic acid sequence hit in the first set of sequence reads is greater than in the second set of sequence reads.

In one embodiment, the in vitro method for discriminating between live and dead microbes in a sample comprises:
(a) sequencing a first and a second set of RNAs extracted from the sample, wherein the first set of RNAs is obtained by culturing the sample in presence of an RNA-labelling agent and the second set of RNAs is obtained by culturing the sample in absence of an RNA-labelling agent, thereby obtaining a first and a second set of sequence reads,
(b) comparing the number of substituted nucleotides in the first set of sequence reads mapping against at least one microbial nucleic acid sequence hit with the number of substituted nucleotides in the second set of sequence reads mapping against said at least one microbial nucleic acid sequence hit, and
(c) concluding that the at least one microbial nucleic acid sequence hit belongs to a live microbe if the number of substituted nucleotides in the sequence reads mapping against the at least one microbial nucleic acid sequence hit in the first set of sequence reads is greater than in the second set of sequence reads.

In one embodiment, the first set of RNAs is obtained by culturing the sample in presence of an RNA-labelling agent, thereby obtaining labelled RNAs, and further submitting said labelled RNAs to nucleotide substitution.

In one embodiment, the in vitro method for discriminating between live and dead microbes in a sample comprises:
(a) sequencing a first and a second set of RNAs extracted from the sample, wherein the first and the second set of RNAs are obtained by culturing the sample in presence of an RNA-labelling agent, thereby obtaining labelled RNAs, and wherein the first set of RNAs is obtained from a first fraction of the labelled RNAs which is submitted to nucleotide substitution, and the second set of RNAs is obtained from a second fraction of the labelled RNAs which is not submitted to nucleotide substitution, thereby obtaining a first and a second set of sequence reads, (b) comparing the number of substituted nucleotides in the first set of sequence reads mapping against at least one microbial nucleic acid sequence hit with the number of substituted nucleotides in the second set of sequence reads mapping against said at least one microbial nucleic acid sequence hit, and (c) concluding that the at least one microbial nucleic acid sequence hit belongs to a live microbe if the number of substituted nucleotides in the sequence reads mapping against the at least one microbial nucleic acid sequence hit in the first set of sequence reads is greater than in the second set of sequence reads.

In one embodiment, the RNA-labelling agent is a thiol-labelled RNA precursor.

In one embodiment, the thiol-labelled RNA precursor is selected from the group comprising 4-thiouridine, 2-thiouridine, 2,4-dithiouridine, 2-thio-4-deoxyuridine, 5-carbethoxy-2-thiouridine, 5-carboxy-2-thiouridine, 5-(n-propyl)-2-thiouridine, 6-methyl-2-thiouridine and 6-(n-propyl)-2-thiouridine, thereby obtaining thiouridine-labelled RNAs.

In one embodiment, the thiol-labelled RNA precursor is preferably 4-thiouridine.

In one embodiment, nucleotide substitution comprises chemically modifying the RNAs, preferably by alkylation, oxidative-nucleophilic-aromatic substitution or osmium-mediated transformation; more preferably by alkylation; and further reverse-transcribing said chemically-modified RNAs.

In one embodiment, the second set of RNAs is obtained by culturing the cell sample in presence of an RNA-labelling agent, thereby obtaining labelled RNAs, and further alkylating said labelled RNAs.

In one embodiment, labelled RNAs are alkylated using an alkylating agent selected from the group comprising iodoacetamide, iodoacetic acid, N-ethylmaleimide and 4-vinylpyridine.

In one embodiment, the alkylating agent is preferably iodoacetamide.

In one embodiment, the step of sequencing RNAs extracted from the cell sample comprises:
(i) reverse-transcribing RNAs, thereby obtaining a cDNA library,
(ii) optionally, amplifying said cDNA library, and
(iii) sequencing said cDNA library, preferably by Next-Generation Sequencing (NGS), deep sequencing or targeted sequencing of custom sequences.

In one embodiment, the step of sequencing RNAs extracted from the cell sample comprises:
(i) reverse-transcribing total RNAs, thereby obtaining a total cDNA library,
(ii) optionally, amplifying said total cDNA library, and
(iii) sequencing said total cDNA library by Next-Generation Sequencing (NGS).

In one embodiment, reverse-transcribing RNAs converts uridine (U) to cytidine (C) instead of uridine (U) to thymidine (T) when the sample was cultured in presence of an RNA-labelling agent and/or when the labelled RNAs are submitted to nucleotide conversion.

In one embodiment, reverse-transcribing total RNAs converts uridine (U) to cytidine (C) instead of uridine (U) to thymidine (T) when the cell sample was cultured in presence of an RNA-labelling agent.

In one embodiment, RNAs undergo first-strand synthesis adenine (A)-to-guanosine (G) substitutions and second-strand synthesis thymidine (T)-to-cytidine (C) substitutions upon reverse-transcription when the sample was cultured in presence of an RNA-labelling agent, preferably a thiol-labelled RNA precursor, and/or when the labelled RNAs are submitted to conditions allowing for nucleotide substitution.

In one embodiment, the step of identifying at least one viral nucleic acid sequence hit mapped against at least one sequence read of the first set of sequence reads comprises:
(i) optionally, filtering the first set of sequence reads,
(ii) optionally, assembling the sequence reads into contigs,
(iii) aligning the sequence reads or contigs onto a database comprising viral nucleic acid sequences,
(iv) identifying the at least one viral nucleic acid sequence hit mapped against at least one sequence read or contig, and
(v) optionally, re-aligning the sequence reads or contigs onto the viral nucleic acid sequence hit identified in step (iv), thereby determining a consensus viral nucleic acid sequence,
thereby identifying at least one consensus viral nucleic acid sequence.

In one embodiment, the at least one microbial nucleic acid sequence hit is identified through:
(i) optionally, filtering the first and/or second set of sequence reads,
(ii) optionally, assembling the sequence reads into contigs,
(iii) aligning the sequence reads or contigs onto a database comprising microbial nucleic acid sequences,
(iv) identifying the at least one microbial nucleic acid sequence hit mapped against at least one sequence read or contig, and
(v) optionally, re-aligning the sequence reads or contigs onto the microbial nucleic acid sequence hit identified in step (iv), thereby determining a consensus microbial nucleic acid sequence,
wherein the consensus microbial nucleic acid sequence corresponds to the microbial nucleic acid sequence hit.

In one embodiment, the at least one microbial nucleic acid sequence hit belongs to a live microbe if:
the number and/or rate of T→C substitutions in the sequence reads mapping against the at least one microbial nucleic acid sequence hit in the first set of sequence reads is greater than the number and/or rate of T→C substitutions in the control sequence; and/or
the number and/or rate of T→C substitutions in the sequence reads mapping against the at least one microbial nucleic acid sequence hit in the first set of sequence reads is greater than the number and/or rate of T→A and/or T→G substitutions in the same sequence reads.

In one embodiment, the at least one viral nucleic acid sequence hit belongs to an infectious virus if the number of T→C substitutions in the sequence reads mapping the at least one identified viral nucleic acid sequence hit in the first set of sequence reads is greater than in the second set of sequence reads.

In one embodiment, the at least one microbial nucleic acid sequence hit belongs to a live microbe if:
the number and/or rate of second-strand synthesis T→C substitutions in the sequence reads mapping against the at least one microbial nucleic acid sequence hit in the first set of sequence reads is greater than the number and/or rate of second-strand synthesis T→C substitutions in the control sequence; and/or the number and/or rate of second-strand synthesis T→C substitutions in the sequence reads mapping against the at least one microbial nucleic acid sequence hit in the first set of sequence reads is greater than the number and/or rate of second-strand synthesis T→A and/or second-strand synthesis T→G substitutions in the same sequence reads.

In one embodiment, the in vitro method according to the present invention comprises the steps of:

(1) (i) sequencing unlabelled total RNAs extracted from the cell sample, wherein unlabelled total RNAs are obtained by culturing the cell sample in absence of an RNA-labelling agent, thereby obtaining a plurality of sequence reads,
   (ii) identifying at least one viral nucleic acid sequence hit mapped against the sequence reads, and
   (iii) determining the number of substituted nucleotides in the sequence reads mapping said identified at least one viral nucleic acid sequence hit; and
(2) (i) sequencing labelled total RNAs extracted from the cell sample, wherein labelled total RNAs are obtained by culturing the cell sample in presence of a labelling agent, thereby obtaining a plurality of sequence reads,
   (ii) determining the number of substituted nucleotides in the sequence reads mapping said identified at least one viral nucleic acid sequence hit,
(3) comparing the number of substituted nucleotides determined in (1)(iii) and (2)(ii), and
(4) concluding that the viral nucleic acid sequence hit belongs to an infectious virus if the number of substituted nucleotides determined in (2)(ii) is greater than the number of substituted nucleotides determined in (1)(iii).

In one embodiment, the microbe is selected from the group comprising viruses, bacteria, archaea, fungi and protozoans.

The present invention also relates to an in vitro method for the diagnosis of a microbial infection in a subject, comprising:
(a) providing a sample from the subject,
(b) performing the in vitro method for discriminating between live and dead microbes on said sample, and
(c) diagnosing the subject as having a microbial infection if the at least one identified microbial nucleic acid sequence hit belongs to a live microbe.

The present invention also relates to an in vitro method for the diagnosis of a viral infection in a subject, comprising:
(a) providing a cell sample from the subject,
(b) performing the in vitro method for discriminating between infectious and non-infectious viral nucleic acid sequences in a cell sample according to the present invention on said cell sample, and
(c) diagnosing the subject as having a viral infection if the at least one identified viral nucleic acid sequence hit belongs to an infectious virus.

The present invention also relates to a method of treating a subject affected with a microbial infection, comprising:
(a) providing a sample from the subject,
(b) performing the in vitro method for discriminating between live and dead microbes on said sample,
(c) diagnosing the subject as having a microbial infection if the at least one identified microbial nucleic acid sequence hit belongs to a live microbe, and
(d) treating the subject if said subject was diagnosed as having a microbial infection in step c).

The present invention also relates to a method for assessing the risk of microbial contamination in a sample, comprising:
(a) providing a sample,
(b) performing the in vitro method for discriminating between live and dead microbes on said sample, and
(c) concluding that the sample is at risk of being contaminated if the at least one identified microbial nucleic acid sequence hit belongs to a live microbe.

BRIEF DESCRIPTION OF THE DRAWINGS

FIGS. 1A and 1B are two graphs illustrating the substitution rates and substitution indexes of T nucleotides. 1A: substitution rates of T nucleotides expressed as the ratio of substituted T to the total of T. 1B: Substitution indexes expressed as the ratio of the "T-to-C" substitution rate to the average of "T-to-A"+"T-to-G" substitution rates. [T: TBEV; S: SMRV; C: cellular RNAs].

DETAILED DESCRIPTION

Figure 2:
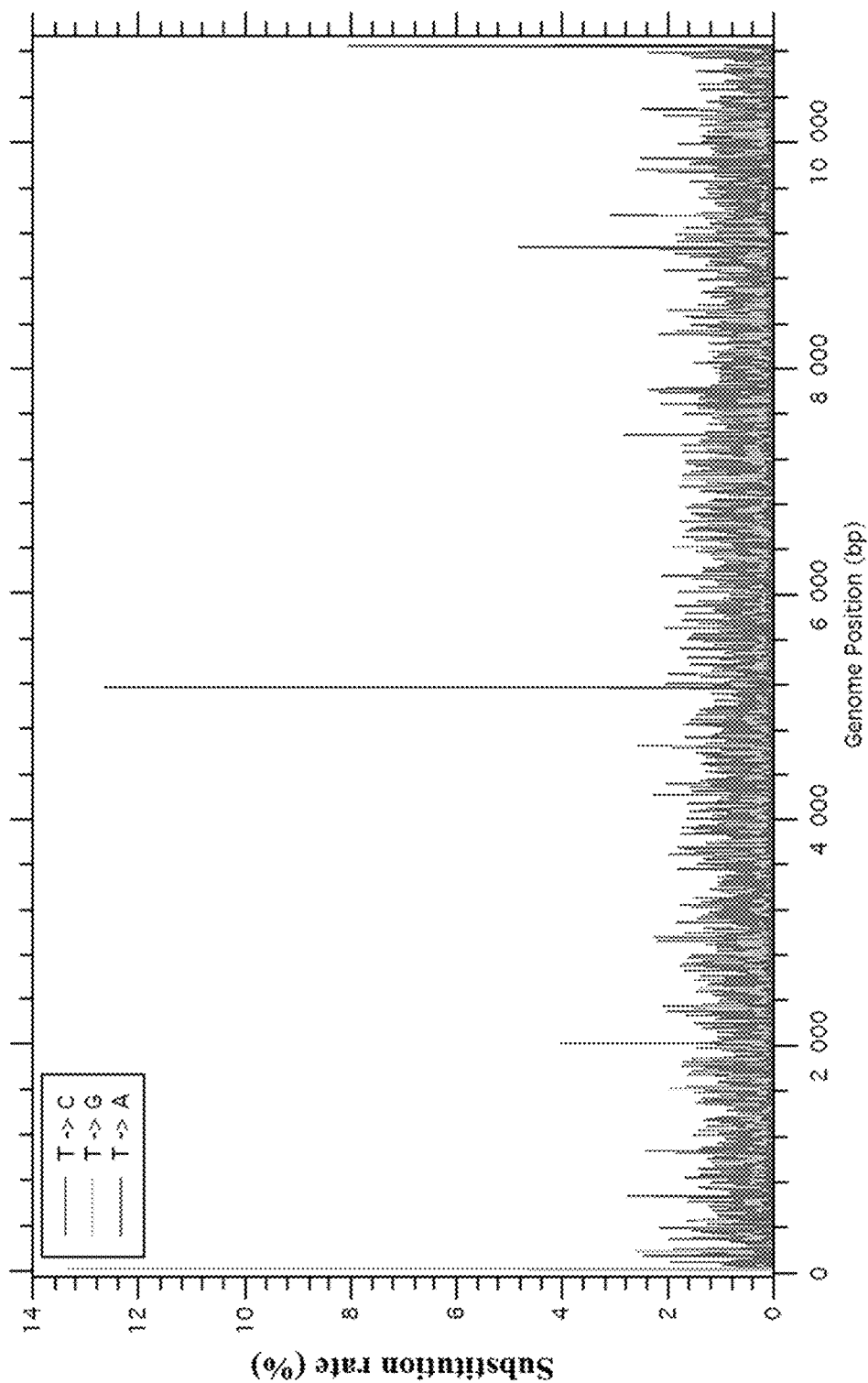
FIG. 2 is a graph illustrating the substitution rates (in %) of T nucleotides to C, G or A, in a sample treated with 4sU and alkylated, using as microbial nucleic acid sequence hit a TBEV consensus sequence built from data of the current condition.

In the present invention, the following terms have the following meanings:

"About" or "approximately", as used herein, can mean within an acceptable error range for the particular value as determined by the one skilled in the art, which will depend in part on how the value is measured or determined, i.e., the limitations of the measurement system. For example, "about" can mean within 1 or more than 1 standard deviation, per the practice in the art. Alternatively, "about" preceding a figure means plus or less 10% of the value of said figure. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

"Amplification", as used herein, refers to the process of producing multiple copies, i.e., at least 2 copies, of a desired template sequence. Techniques to amplify nucleic acids are well-known to the one skilled in the art, and include specific amplification methods as well as random amplification methods.

"Biological sample", as used herein, refers herein to any sample that is obtained from, obtainable from, or otherwise derived from a subject. "Biological samples" encompass "solid tissue samples" and "fluid samples". The term "solid tissue sample" refers herein to a sample of solid tissue isolated from anywhere in the body. Tissue samples comprise cells that are not disaggregated, and which occur in large clusters. Examples of tissue samples include, but are not limited to, biopsy specimens and autopsy specimens. The term "fluid sample" refers herein to a sample of fluid isolated from anywhere in the body. Examples of fluid samples include, but are not limited to, serum, plasma, whole blood, urine, saliva, breast milk, tears, sweat, joint fluid, cerebrospinal fluid, lymph fluid, sputum, mucus, pelvic fluid, synovial fluid, body cavity washes, eye brushings, skin scrapings, buccal swabs, vaginal swabs, pap smears, rectal swabs, aspirates, semen, vaginal fluid, ascitic fluid and amniotic fluid. In a preferred embodiment, the "biological sample" is a cell sample, i.e., any biological sample as described herein, comprising at least one cell.

"cDNA library", as used herein, refers to a library composed of complementary DNAs which are reverse-transcribed from mRNAs.

"Contig", as used herein, refers to overlapping sequence reads. Typically, a contig is a continuous nucleic acid sequence resulting from the reassembly of the small DNA fragments (sequence reads) generated by next-generation sequencing. Practically, assembly software will search for pairs of overlapping sequence reads. Optionally, the assembly software can access nucleic acid or amino acid databases to "align and check", thereby validating the sequence read assembly. Assembling the sequences from pairs of overlapping sequence reads produces a longer contiguous read (contig) of sequenced DNA. By repeating this process multiple times, at first with the initial short pairs of sequence reads, then using increasingly longer pairs that are the result of previous assembly, longer contigs can be determined.

"Deep sequencing", as used herein, refers to nucleic acid sequencing to a depth that allows each base to be read multiple times from independent nucleic acid molecules (e.g., a large number of template molecules is sequenced relative to the length of the sequence) and allows sequencing of thousands of molecules simultaneously, thereby allowing to characterize complex pools of nucleic acid molecules and increasing sequencing accuracy. Deep sequencing of the transcriptome, also known as RNA-Seq, provides both the sequence and frequency of contained RNA molecule species that are present at any particular time in a specific sample.

"Expected value" or "e-value", as used herein, refers to a parameter that describes the number of sequence hits one can expect to see "by chance" when aligning sequence reads or contigs on a database of a particular size. The e-value decreases exponentially as the score of the match increases. Essentially, the e-value describes the random background noise. For example, an e-value of 1 assigned to a hit can be interpreted as meaning that, in a database of the current size, one might expect to see 1 match with a similar score simply by chance. The lower the e-value, or the closer it is to zero, the more "significant" the match is.

"Live microbe", as used herein, refers to any microbe which is transcriptionally active, i.e., which is able to synthetize, either by itself (such as in the case of bacteria, archaea, fungi or protozoans for example) or after infecting a host cell (such as in the case of viruses for example), RNAs. Live microbes include latent microbes, i.e., dormant microbes which can reactivate. It is to be noted that latent microbes, although dormant, exhibit a basal transcriptional activity. By contract, a "dead microbe" refers to a microbe which is not transcriptionally active, i.e., for which no transcribed gene is detectable. In the context of the present invention, the method aims at distinguishing between live microbes and inert microbial nucleic acid sequences, either free in the sample or contained inside a so-called dead microbe.

"Lysate", as used herein, refers to a liquid or solid collection of materials following a lysis procedure.

"Lysis" (noun) or "lyse" (verb), as used herein, refer to the disruption of (or the action of disrupting) a biological sample in order to gain access to materials that are otherwise inaccessible. When the biological sample is a cell, lysis refers to breaking the cellular membrane of the cell, causing the cellular contents to spill out. Lysis methods are well-known to the one skilled in the art, and include, but are not limited to, proteolytic lysis, chemical lysis, thermal lysis, mechanical lysis and osmotic lysis.

"Nucleic acid sequence primer" or "primer", as used herein, refer to an oligonucleotide that is capable of hybridizing or annealing with a nucleic acid sequence and serving as an initiation site for nucleotide polymerization under appropriate conditions, such as the presence of nucleoside triphosphates and an enzyme for polymerization, such as DNA or RNA polymerase or reverse transcriptase, in an appropriate buffer and at a suitable temperature.

"Oligonucleotide", as used herein, refers to a polymer of nucleotides, generally to a single-stranded polymer of nucleotides. In some embodiments, the oligonucleotide comprises from 2 to 500 nucleotides, preferably from 10 to 150 nucleotides, preferably from 20 to 100 nucleotides. Oligonucleotides may be synthetic or may be made enzymatically. In some embodiments, oligonucleotides may comprise ribonucleotide monomers, deoxyribonucleotide monomers, or a mix of both.

"Microbe" or "microorganism", as used herein, refer to an organism, such as, without limitation, a virus, a bacterium, an archaeon, a fungus or a protozoan, likely able of infecting or contaminating a sample; and/or of generating, transmitting or carrying a disease in a subject.

"Polymerase chain reaction" or "PCR", as used herein, encompass methods including, but not limited to, allele-specific PCR, asymmetric PCR, hot-start PCR, intersequence-specific PCR, methylation-specific PCR, miniprimer PCR, multiplex ligation-dependent probe amplification, multiplex-PCR, nested PCR1 quantitative PCR, reverse transcription PCR and/or touchdown PCR. DNA polymerase enzymes suitable to amplify nucleic acids comprise, but are not limited to, Taq polymerase Stoffel fragment, Taq polymerase, Advantage DNA polymerase, AmpliTaq, AmpliTaq Gold, Titanium Taq polymerase, KlenTaq DNA polymerase, Platinum Taq polymerase, Accuprime Taq polymerase, Pfu polymerase, Pfu polymerase turbo, Vent polymerase, Vent exo-polymerase, Pwo polymerase, 9 Nm DNA polymerase, Therminator, Pfx DNA polymerase, Expand DNA polymerase, rTth DNA polymerase, DyNAzyme-EXT Polymerase, Klenow fragment, DNA polymerase I, T7 polymerase, Sequenase™, Tfi polymerase, T4 DNA polymerase, Bst polymerase, Bca polymerase, BSU polymerase, phi-29

DNA polymerase and DNA polymerase Beta or modified versions thereof. In one embodiment, the DNA polymerase has a 3'-5' proofreading, i.e., exonuclease, activity. In one embodiment, the DNA polymerase has a 5'-3' proofreading, i.e., exonuclease, activity. In one embodiment, the DNA polymerase has strand displacement activity, i.e., the DNA polymerase causes the dissociation of a paired nucleic acid from its complementary strand in a direction from 5' towards 3', in conjunction with, and close to, the template-dependent nucleic acid synthesis. DNA polymerases such as E. coli DNA polymerase I, Klenow fragment of DNA polymerase I, T7 or T5 bacteriophage DNA polymerase, and HIV virus reverse transcriptase are enzymes which possess both the polymerase activity and the strand displacement activity. Agents such as helicases can be used in conjunction with inducing agents which do not possess strand displacement activity in order to produce the strand displacement effect, that is to say the displacement of a nucleic acid coupled to the synthesis of a nucleic acid of the same sequence. Likewise, proteins such as Rec A or Single Strand Binding Protein from E. coli or from another organism could be used to produce or to promote the strand displacement, in conjunction with other inducing agents (Kornberg & Baker (1992). Chapters 4-6. In DNA replication (2nd ed., pp. 113-225). New York: W.H. Freeman).

"Random amplification techniques", as used herein, means amplification of any nucleic acid present in a biological sample, independently of its sequence. This includes without limitation, multiple displacement amplification (MDA), random PCR, random amplification of polymorphic DNA (RAPD) or multiple annealing and looping based amplification cycles (MALBAC).

"Transcriptionally-active microbial nucleic acid sequence", as used herein, refers to a nucleic acid sequence belonging to a live microbe, i.e., a microbe expressing microbial genes, even if the microbe is latent. By contrast, "inert microbial nucleic acid sequence", as used herein, refers to a nucleic acid sequence belonging to an inactive microbe, i.e., a dead microbe. The term "inert microbial nucleic acid sequence" further refers to free nucleic acid sequences, i.e., outside of a microbe, whether intact or degraded/fragmented, but in any case, not active.

"Transcriptionally-active viral nucleic acid sequence", as used herein, refers to a nucleic acid sequence belonging to an active virus, i.e., a live virus expressing viral genes, even if the virus cycle is abortive, i.e., does not lead to the formation of virus particles (such as in the case, e.g., of latent viruses). By contrast, "inert viral nucleic acid sequence", as used herein, refers to a nucleic acid sequence belonging to an inactive virus, i.e., a dead virus or nucleic acids not associated to virus particles.

"Reverse transcription", as used herein, refers to the replication of RNA using an RNA-directed DNA polymerase (reverse transcriptase, abbreviated "RT") to produce complementary strands of DNA ("cDNA"). The reverse-transcription of RNAs may be carried out by techniques well-known to the one skilled in the art, using a reverse transcriptase enzyme and a mix of 4 deoxyribonucleotides triphosphate (dNTPs), namely deoxyadenosine triphosphate (dATP), deoxycytidine triphosphate (dCTP), deoxyguanosine triphosphate (dGTP) and (deoxy)thymidine triphosphate (dTTP). In some embodiments, the reverse-transcription of RNAs comprises a first step of first-strand cDNA synthesis. Methods for first-strand cDNA synthesis are well-known to the one skilled in the art. First-strand cDNA synthesis reactions can use a combination of sequence-specific primers, oligo(dT) primers or random primers. Examples of reverse transcriptase enzymes include, but are not limited to, M-MLV reverse transcriptase, SuperScript II (Invitrogen), SuperScript III (Invitrogen), SuperScript IV (Invitrogen), Maxima (ThermoFisher Scientific), ProtoScript II (New England Biolabs), PrimeScript (ClonTech).

"Sequence read", as used herein, refers to a sequence or data representing a sequence of nucleotide bases, in other words, the order of monomers in a nucleic acid sequence, which is determined by a sequencer.

"Sequencer" or "sequenator", as used herein, refer to apparatus used for determining the order of constituents in a biological polymer, such as a nucleic acid or a protein. Preferably, sequencers, in the sense of the present invention, refer to next-generation sequencers. A "next-generation sequencer" can include a number of different sequencers based on different technologies, such as Illumina sequencing, Roche 454 sequencing, Ion torrent sequencing, SOLiD sequencing and the like.

"Subject", as used herein, refers to a mammal, preferably a human. In one embodiment, the subject is a pet, including, without limitation, a dog, a cat, a guinea pig, a hamster, a rat, a mouse, a ferret, a rabbit, a bird or an amphibian. In one embodiment, a subject may be a "patient", i.e., a female or a male, an adult or a child, who/which is awaiting the receipt of, or is receiving medical care or was/is/will be the object of a medical procedure, or is monitored for the development of a disease, disorder or condition, in particular a viral, bacterial, archaeal, fungal or protozoan infection.

"Template" or "template sequence", as used herein, refer to a nucleic acid sequence for which amplification is desired. A template can comprise DNA or RNA. In one embodiment, the template sequence is known. In one embodiment, the template sequence is not known.

The terminology used herein is for the purpose of describing particular cases only and is not intended to be limiting. As used herein, the singular forms "a", "an" and "the" are intended to include the plural forms as well, unless the context clearly indicates otherwise.

Furthermore, to the extent that the terms "including", "includes", "having", "has", "with", or variants thereof are used in either the detailed description and/or the claims, such terms are intended to be inclusive in a manner similar to the term "comprising".

The present invention relates to a method for discriminating between live and dead microbes in a sample, preferably a cell sample. In particular, the method according to the present invention is based on the discrimination between transcriptionally-active and inert microbial nucleic acid sequences in a sample, preferably a cell sample.

The method of the present invention is particularly useful for distinguishing between (1) dead microbes—such as viruses, bacteria, archaea, fungi or protozoans—and inert microbial sequences; and (2) active (or transcriptionally-active) and latent microbes—such as viruses, bacteria, archaea, fungi or protozoans.

It is therefore to be understood that the present method is readily applicable to the detection of any sort of microbe, and the discrimination between live and dead microbes.

In one embodiment, the microbe is selected from viruses, bacteria, archaea, fungi and protozoans.

In one embodiment, the microbe is a virus.

Viruses are small infectious agents that replicates inside living cells, and which infect all types of life form.

The Baltimore classification of viruses is based on the mechanism of mRNA production. Viruses must generate mRNAs from their genomes to produce proteins and replicate themselves, but different mechanisms are used to achieve this in each virus family Viral genomes may be single-stranded (ss) or double-stranded (ds), RNA or DNA, and may or may not use reverse-transcriptase. In addition, ssRNA viruses may be either sense (+) or antisense (−). This classification places viruses into seven groups:

I. dsDNA viruses (such as, e.g., adenoviruses, herpesviruses or poxviruses),
II. (+)ssDNA viruses (such as, e.g., anelloviridae, bidnaviridae, circoviridae, geminiviridae, genomoviridae, inoviridae, microviridae, nanoviridae, parvoviridae, smacoviridae or spiraviridae),
III. dsRNA viruses (such as, e.g., reoviruses),
IV. (+)ssRNA viruses (such as, e.g., picornaviruses or togaviruses),
V. (−)ssRNA viruses (such as, e.g., orthomyxoviruses, rhabdoviruses),
VI. (+)ssRNA-RT viruses with DNA intermediate in life-cycle (such as, e.g., retroviruses),
VII. dsDNA-RT viruses DNA with RNA intermediate in life-cycle (such as, e.g., hepadnaviruses).

In one embodiment, the method according to the present invention is for discriminating samples, preferably cell samples, containing transcriptionally-active and inert viral nucleic acid sequences belonging to viruses selected from the group comprising or consisting of dsDNA viruses, (+)ssDNA viruses, dsRNA viruses, (+)ssRNA viruses, (−)ssRNA viruses, (+)ssRNA-RT viruses and dsDNA-RT viruses.

In one embodiment, the method according to the present invention is for discriminating samples, preferably cell samples, containing transcriptionally-active and inert viral nucleic acid sequences belonging to viruses selected from those disclosed in the International Committee on Taxonomy of Viruses (ICTV) database, preferably in the ICTV Master Species List 2018b.v2 of May 31, 2019 (MSL #34), which is herein incorporated by reference in its entirety.

In one embodiment, the microbe is a bacterium.

In one embodiment, the method according to the present invention is for discriminating samples, preferably cell samples, containing transcriptionally-active and inert bacterial nucleic acid sequences belonging to bacteria.

Examples of bacteria include, but are not limited to, bacteria belonging to the Acidobacteria, Actinobacteria, Aquificae, Bacteroidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae and Verrucomicrobia phyla; including subtaxons thereof.

In a preferred embodiment, the bacterium is a Firmicute, preferably of the Bacilli class, more preferably of the Mollicute subclass, even more preferably of *Mycoplasma* genus.

In one embodiment, the microbe is an archaeon.

In one embodiment, the method according to the present invention is for discriminating samples, preferably cell samples, containing transcriptionally-active and inert archaeal nucleic acid sequences belonging to archaea.

Examples of archaea include, but are not limited to, archaea belonging to the Aenigmarchaeota, Aigarchaeota, Altiarchaeia, Archaeoglobi, Asgardarchaeota, Bathyarchaeota, Crenarchaeota, Diapherotrites, Geoarchaeota, Halobacteria, Korarchaeota, Methanobacteria, Methanococci, Methanomicrobia, Methanopyri, Nanoarchaeota, Nanohaloarchaea, Parvarchaeota, Thalassoarchaeia, Thaumarchaeota, Thermococci, Thermoplasmata and Woesearchaeota phyla; including subtaxons thereof.

In one embodiment, the microbe is a fungus.

Fungi are eukaryotic organisms, including yeasts and molds, characterized in that they comprise chitin in their cell walls.

In one embodiment, the method according to the present invention is for discriminating samples, preferably cell samples, containing transcriptionally-active and inert fungal nucleic acid sequences belonging to fungi.

Examples of fungi include, but are not limited to, fungi belonging to the Ascomycota, Basidiomycota, Entorrhizomycota, Glomeromycota, Mucoromycota, Calcarisporiellomycota, Mortierellomycota, Kickxellomycota, Entomophthoromycota, Olpidiomycota, Basidiobolomycota, Neocallimastigomycota, Chytridiomycota and Blastocladiomycota phyla; including subtaxons thereof.

In one embodiment, the microbe is a protozoan.

In one embodiment, the method according to the present invention is for discriminating samples, preferably cell samples, containing transcriptionally-active and inert protozoan nucleic acid sequences belonging to protozoans.

Examples of protozoans include, but are not limited to, protozoans belonging to the Euglenozoa, Amoebozoa, Choanozoa, Microsporidia and Sulcozoa phyla; including subtaxons thereof.

In one embodiment, the sample is a biological sample. Examples of suitable biological samples include, but are not limited to, solid tissue samples and fluid samples.

In one embodiment, the biological sample is/was obtained through sampling by minimally invasive or non-invasive approaches.

In one embodiment, the biological sample was previously obtained from the subject, i.e., the methods according to the present invention are in vitro methods.

In one embodiment, the biological sample is a cell sample. By "cell sample", it is referred to any biological sample as described herein, comprising at least one cell.

In one embodiment, the biological sample is cultured. Therefore, encompassed under the term "biological sample" are cell or tissue cultures, preferably in vitro cell or tissue cultures, such as, e.g., a culture of cells or tissues isolated from a cytology sample, a tissue sample or a biological fluid sample.

In one embodiment, the method according to the present invention comprises an initial step of culturing the sample, preferably the cell sample, preferably culturing in vitro the cell sample.

The culture of cell samples, in particular the culture of cells or tissues isolated from a cytology sample, a tissue sample or a biological fluid sample, is well known to the one skilled in the art.

In one embodiment, the cell sample is seeded in a density that allows exponential growth. In one embodiment, the biological sample is seeded at about 50% to about 80% confluency.

The initial step of culturing the sample is required (1) to allow the potential microbe (such as the virus, bacterium, archaeon, fungus or protozoan) in the sample to transcribe RNAs (which is the key biological process used in the present method to discriminate between live and dead microbes) and (2) for metabolic labelling. In the case where the microbe to be detected is not a self-replicating microbe (such as, e.g., a virus, or some bacterias such as *Mycoplasma*), the sample shall be a cell sample to allow the potential microbe to infect said cells and replicate. In the case where the microbe is a self-replicating microbe (i.e., the microbe comprises or is itself a cell, such as, typically, a bacterium, an archaeon, a fungus or a protozoan), it is not compulsory that the sample be a cell sample.

In one embodiment, the sample is not a biological sample. In this case, the sample may be, e.g., an environmental sample such as water, soil, air, and the like. Other examples of non-biological samples include food samples. Other examples of non-biological sample include preservation medium.

In one embodiment, the method for discriminating between live and dead microbes—preferably virus, bacterium, archaeon, fungus or protozoan—in a sample, preferably a cell sample, comprising discriminating between transcriptionally-active and inert microbial—preferably viral, bacterial, archaeal, fungal or protozoan—nucleic acid sequences in the sample, preferably the cell sample, comprises the steps of:

(a) sequencing a first set of RNAs extracted from the sample, preferably the cell sample, wherein the first set of RNAs is obtained by culturing the sample, preferably the cell sample, in presence of an RNA-labelling agent and further by submitting the extracted RNAs to conditions allowing for nucleotide substitution; thereby obtaining a first set of sequence reads;

(b) comparing the number of substituted nucleotides in the first set of sequence reads mapping against at least one microbial—preferably viral, bacterial, archaeal, fungal or protozoan—nucleic acid sequence hit with a control sequence; and (c) concluding that the at least one microbial—preferably viral, bacterial, archaeal, fungal or protozoan—nucleic acid sequence hit belongs to a live microbe—preferably virus, bacterium, archaeon, fungus or protozoan—if the number of substituted nucleotides in the sequence reads mapping against said at least one microbial—preferably viral, bacterial, archaeal, fungal or protozoan—nucleic acid sequence hit in the first set of sequence reads is greater than the number of nucleotides randomly substituted in the control sequence.

In one embodiment, the method of the invention is carried out in conditions causing a reverse-transcriptase enzyme to make errors (i.e., to incorporate mispaired nucleotides) that can be detected and compared, by reference to a consensus standard method of reverse-transcription. Such conditions include the presence, in the RNAs to be reverse-transcribed, of labels such as thiol labels, and/or of nucleotide modifications by nucleotide substitution techniques. Exemplary conditions are further detailed in the following.

As used herein, the term "mispaired nucleotide" refers to a nucleotide that is incorporated in a non-Watson-Crick base pairing fashion.

In one embodiment, the error rate of the reverse-transcriptase enzyme is not linked to the fidelity of the reverse-transcriptase enzyme fidelity.

As used herein, the term "fidelity" with reference of a reverse-transcriptase enzyme refers to the sequence accuracy maintained by the enzyme during synthesis of DNA from RNA. Fidelity is inversely correlated to the error rate of reverse-transcription.

In one embodiment, the method according to the present invention comprises a step of sequencing a first set of RNAs extracted from the sample, preferably the cell sample. In one embodiment, the method according to the present invention comprises a step of sequencing a first set of total RNAs extracted from the sample, preferably the cell sample. In one embodiment, the method according to the present invention comprises a step of sequencing a first set of total messenger RNAs (mRNAs) extracted from the sample, preferably the cell sample.

In one embodiment, the step of sequencing a first set of RNAs extracted from the sample, preferably the cell sample, comprises one or more or all of the sub-steps of labelling RNAs, lysing the cells, extracting RNAs, substituting nucleotides in labelled RNAs, generating a cDNA library, amplifying the cDNA library and sequencing the cDNA library.

Labelling RNA is typically carried out in culture, during in vitro transcription, by addition in the culture medium of a label to be incorporated in RNA transcripts, thereby obtaining labelled RNAs. Alternatively or additionally, labelling RNA can also be carried out in culture without addition of a label to be incorporated in RNA transcripts, in the case where the sample from which the RNAs are extracted already comprise such label, as will be further detailed below.

By "RNA transcript", it is meant any neosynthesized RNA molecule.

The labelling of RNA transcripts can be carried out by technics well-known to the one skilled in the art. Such technics include, but are not limited to, those described in Schulz & Rentmeister (2014. Chembiochem. 15(16):2342-7), Huang & Yu (2013. Curr Protoc Mol Biol. Chapter 4:Unit4.15) and Liu et al. (2016. Bioessays. 38(2):192-200).

Preferably, metabolic labelling of RNAs alters Watson-Crick base pairing and causes reverse-transcription of labelled RNAs to substitute nucleotides, i.e., to pair a labelled nucleotide with a non-Watson-Crick nucleotide. For example, a labelled uridine may be paired with a guanosine instead of an adenine during first-strand synthesis. Consequently, a cytosine shall be incorporated during second-strand synthesis, ultimately leading to a thymidine (T) to cytosine (C) substitution with respect to the initial nucleic acid sequence.

In one embodiment, the metabolic labelling of RNA transcripts is carried out by thiol-labelling. Thiol-labelling is a technic well-known in the art, which comprises the incorporation of thiol-labelled RNA precursors into newly synthesized RNAs. Such technics include, but are not limited to, those described in Cleary et al. (2005. Nat Biotechnol. 23(2):232-7), Miller et al. (2009. Nat Methods. 6(6):439-41), Garibaldi et al. (2017. Methods Mol Biol. 1648:169-176), Russo et al. (2017. Methods. 120:39-48) and Herzog et al. (2017. Nat Methods. 14(12):1198-1204).

Examples of suitable thiol-labelled RNA precursors include, but are not limited to, 4-thiouridine, 2-thiouridine, 2,4-dithiouridine, 2-thio-4-deoxyuridine, 5-carbethoxy-2-thiouridine, 5-carboxy-2-thiouridine, 5-(n-propyl)-2-thiouridine, 6-methyl-2-thiouridine, 6-(n-propyl)-2-thiouridine, 6-thioguanosine, 6-methylthioguanosine, 6-thioinosine and 6-methylthioinosine.

In one embodiment, the thiol-labelled RNA precursor is a thiouridine derivative, preferably selected from the group comprising or consisting of 4-thiouridine (4sU), 2-thiouridine (2sU), 2,4-dithiouridine (2.4sU), 2-thio-4-deoxyuridine, 5-carbethoxy-2-thiouridine, 5-carboxy-2-thiouridine, 5-(n-propyl)-2-thiouridine, 6-methyl-2-thiouridine and 6-(n-propyl)-2-thiouridine.

In a preferred embodiment, the thiol-labelled RNA precursor is 4-thiouridine (sometimes abbreviated as "4sU" or "s4U").

In one embodiment, the thiol-labelled RNA precursor is supplied to the sample, preferably the cell sample, from the culture medium. In one embodiment, the thiol-labelled RNA precursor is added in the culture medium.

Thiol-labelled RNA precursors, when added to the culture medium, can be imported into cells of the sample, preferably the cell sample, (such as, e.g., cells infected by a virus or microbes comprising or being themselves a cell, e.g., a bacterium, a fungus or a protozoan) through specific transporters, named "Equilibrative Nucleoside Transporters". These transporters are quasi-ubiquitous in metazoans. In particular, 4-thiouridine can be imported into cells through the Equilibrative Nucleoside Transporter 1 (ENT1), encoded in humans by the SLC29A1 gene.

In one embodiment, fresh thiol-labelled RNA precursor is added to the culture every 1 hour, 2 hours, 3 hours, 4 hours, 5 hours, 6 hours or more.

In one embodiment, the sample, preferably the cell sample, is cultured in a thiol-labelled RNA precursor-containing culture medium for a period of time ranging from about 2 hours to about 15 hours, preferably from about 4 hours to about 12 hours, preferably from about 6 hours to about 10 hours.

In one embodiment, the sample, preferably the cell sample, is cultured in a thiol-labelled RNA precursor-containing culture medium for a first period of time and a second period of time, comprising addition of fresh thiol-labelled RNA precursor between the first and the second period of time. In one embodiment, the first period of time ranges from about 1 hour to about 10 hours, preferably from about 2 hours to about 8 hours, preferably from about 4 hours to about 6 hours, preferably is about 6 hours. In one embodiment, the second period of time ranges from about 1 hour to about 6 hours, preferably from about 2 hours to about 5 hours, preferably from about 3 hours to about 4 hours, preferably is about 3 hours.

Preferably, the thiol-labelled RNA precursor is not toxic to the sample, preferably the cell sample.

In one embodiment, the thiol-labelled RNA precursor is supplied to the sample, preferably the cell sample, at a concentration which does not compromise cell viability. In one embodiment, a "concentration which does not compromise cell viability" ranges from about 1 µM to about 2 mM final, preferably from about 10 µM to about 1.5 mM final, preferably from about 100 µM to about 1 mM final, preferably from about 250 µM to about 1 mM final, preferably from about 500 µM to about 1 mM final, preferably from about 700 µM to about 900 µM final, preferably about 800 µM final of thiol-labelled RNA precursor.

In one embodiment, the thiol-labelled RNA precursor is supplied to the sample, preferably the cell sample, directly from the microbe—preferably the virus, bacterium, archaeon, fungus or protozoan. In one embodiment, the thiol-labelled RNA precursor is not added in the culture medium.

Certain microbes are able to catalyze the biosynthesis of thiol-labelled RNA precursors, using enzymes such as, without limitation, 4-thiouridine synthetase (ThiI) (Mueller et al., 1998. *Nucleic Acids Res.* 26(11):2606-10) or 2-thiouridine synthetase (MnmA) (Kambampati & Lauhon, 2003. *Biochemistry.* 42(4):1109-1; Black & Dos Santos, 2015. *J Bacteriol.* 197(11):1952-62).

In a specific embodiment where the sample comprises a microbe able to catalyze the biosynthesis of thiol-labelled RNA precursors, it can be advantageous to further supply the thiol-labelled RNA precursor to the sample, preferably the cell sample, from the culture medium.

In this embodiment, the thiol-labelled RNA precursor further supplied from the culture medium may be the same or may be different from the thiol-labelled RNA precursor supplied by the microbe.

In this embodiment, the thiol-labelled RNA precursor further supplied from the culture medium may be supplied as described hereinabove (with regards to, without limitation, addition of fresh thiol-labelled RNA precursor, concentration, periods of time, etc.).

Thiol-labelled RNA precursors and thiol-labelled RNAs are light-sensitive, and prone to oxidation. Therefore, in one embodiment, RNA labelling is carried out in the dark, or, at the very least, with protection from light. In one embodiment, RNA labelling is carried out in presence of a reducing agent. Examples of suitable reducing agents include, but are not limited to, β-mercaptoethanol, dithiothreitol (DTT), tris(2-carboxyethyl)phosphine (TCEP), cysteine, N-acetyl cysteine, cysteamine, 2-mercaptoethanesulfonic acid sodium salt, dithioerythritol (DTE) and bis(2-mercaptoethyl)sulfone).

Typically, lysing the cells of the sample, preferably the cell sample, aims at releasing the cell's content, in particular, its RNAs. In one embodiment, lysing the cells of the sample may be optional, such as in the case where the RNA content of the cells is already released in the sample.

In one embodiment, cells are lysed by chemical lysis, mechanical lysis, proteolytic lysis, thermal lysis and/or osmotic lysis. These cell lysis technics are well-known to the one skilled in the art.

In one embodiment, cells are lysed in a suitable lysis solution. Lysis solutions can comprise various components, including salts, buffers, detergents, reducing agents, protease inhibitors, nuclease inhibitors, glycerol, sugars and the like. The one skilled in the art has knowledge in lysis solutions and is readily able to design and/or choose the appropriate lysis solution depending on the type of cells to lyse.

In one embodiment, cell lysis is carried out in presence of ribonuclease (RNase) inhibitor. RNases can sometimes be released from cells during cell lysis, or be co-purified with isolated RNA, and therefore compromise downstream applications. Such RNase contamination can also be introduced via tips, tubes and other reagents used in procedures. RNase inhibitors are commercially available.

Thiol-labelled RNAs being light-sensitive and prone to oxidation, in one embodiment, cell lysis is carried out in the dark, or, at the very least, with protection from light. In one embodiment, cell lysis is carried out in presence of a reducing agent. Examples of suitable reducing agents include, but are not limited to, β-mercaptoethanol, dithiothreitol (DTT), tris(2-carboxyethyl)phosphine (TCEP), cysteine, N-acetyl cysteine, cysteamine, 2-mercaptoethanesulfonic acid sodium salt, dithioerythritol (DTE) and bis(2-mercaptoethyl)sulfone).

Extracting RNAs can be carried out by technics well-known to the one skilled in the art. Such technics include, but are not limited to, chloroform-isoamyl alcohol extraction, phenol-chloroform extraction, alkaline extraction, guanidinium thiocyanate-phenol-chloroform extraction, binding on anion exchange resin, silica matrices, glass particle, diatomaceous earth, magnetic particles made from different synthetic polymers, biopolymers, porous glass and based on inorganic magnetic.

Preferably, extraction of RNAs is carried out by chloroform-isoamyl alcohol extraction, using, e.g., chloroform: isoamyl alcohol 24:1.

In one embodiment, extracted RNAs are further precipitated. Precipitating RNAs can be carried out by technics well-known to the one skilled in the art. Such technics include isopropanol-ethanol precipitation, TRIzol method (Chomczynski, 1993. *Biotechniques*. 15(3):532-4, 536-7) and Pine Tree method (Chang et al., 1993. *Plant Mol Biol Report*. 11(2):113-116).

Preferably, precipitation of RNAs is carried out by isopropanol-ethanol precipitation.

Thiol-labelled RNAs being light-sensitive and prone to oxidation, in one embodiment, extraction of RNAs is carried out in the dark, or, at the very least, with protection from light. In one embodiment, extraction of RNAs is carried out in presence of a reducing agent. Examples of suitable reducing agents include, but are not limited to, β-mercaptoethanol, dithiothreitol (DTT), tris(2-carboxyethyl)phosphine (TCEP), cysteine, N-acetyl cysteine, cysteamine, 2-mercaptoethanesulfonic acid sodium salt, dithioerythritol (DTE) and bis(2-mercaptoethyl)sulfone).

In one embodiment, labelled RNAs undergo nucleotide substitution. In one embodiment, labelled RNAs are submitted to conditions allowing for nucleotide substitution.

In the following, the terms "substitution", "conversion", "transformation", may be used interchangeably to refer to the incorporation of mispaired nucleotides.

Nucleotide substitution in labelled RNAs can be carried out by chemically modifying the labelled RNAs; and further reverse-transcribing said chemically-modified labelled RNAs. Accordingly, conditions allowing for nucleotide substitution include a chemical modification of the labelled RNAs; and the reverse-transcription of said chemically-modified labelled RNAs.

Preferably, methods of nucleotide conversion allow to alter Watson-Crick base pairing in labelled RNAs, and causes reverse-transcription of labelled RNAs during cDNA synthesis to incorporate mispaired nucleotides, i.e., to pair a labelled nucleotide with a non-Watson-Crick nucleotide.

For example, a labelled uridine (such as, a thiol-labelled uridine) may be paired with a guanosine (G) instead of an adenine (A) during cDNA first-strand synthesis. Consequently, a cytosine shall be incorporated during second-strand synthesis, ultimately leading to a thymidine (T) to cytosine (C) substitution with respect to the initial nucleic acid sequence.

Nucleotide substitution can therefore be defined as the equivalent first-strand synthesis nucleotide substitution (i.e., the nucleotide substitution occurring upon first-strand synthesis); or as the equivalent second-strand synthesis nucleotide substitution (i.e., the nucleotide substitution occurring upon second-strand synthesis).

In one embodiment, labelled RNAs undergo a first-strand synthesis A-to-G (A→G) substitution. In one embodiment, labelled RNAs undergo a second-strand synthesis T-to-C (T→C) substitution. In these embodiments, a labelled uridine (U) in the labelled RNA is therefore converted to cytosine (C) instead of thymidine (T) in the corresponding cDNA.

Unless explicitly stated otherwise, nucleotide substitutions recited herein correspond to second-strand synthesis nucleotide substitutions.

Suitable chemical modifications of labelled RNAs include, but are not limited to, alkylation, oxidative-nucleophilic-aromatic substitution, osmium-mediated transformation, or any other method known to the one skilled in the art.

Alkylating labelled RNAs can be carried out by technics well-known to the one skilled in the art. Such technics include, but are not limited to, those described in Herzog et al. (2017. *Nat Methods*. 14(12):1198-1204).

Preferably, alkylation of labelled RNAs is carried out after extraction of RNAs as detailed hereinabove.

In one embodiment, labelled RNA alkylation is carried out using an alkylating agent. Examples of suitable alkylating agents include, but are not limited to, iodoacetamide, iodoacetic acid, N-ethylmaleimide and 4-vinylpyridine.

In a preferred embodiment, the alkylating agent is iodoacetamide.

A non-limiting example of alkylation treatment of labelled RNAs comprises adding to labelled RNAs:
from about 1 mM final to about 20 mM final, preferably from about 5 mM final to about 15 mM final, preferably about 10 mM final of iodoacetamide in 100% ethanol,
from about 10 mM final to about 100 mM final, preferably from about 25 mM final to about 75 mM final, preferably about 50 mM final of a buffer at pH 8.0 (such as, e.g., a sodium phosphate ($NaPO_4$) buffer),
from about 25% v/v to about 75% v/v, preferably from about 40% v/v to about 60% v/v, preferably about 50% v/v of DMSO.

Thiol-labelled RNAs being light-sensitive, in one embodiment, RNA alkylation is carried out in the dark, or, at the very least, with protection from light.

In one embodiment, RNA alkylation is not carried out in presence of a reducing agent.

In one embodiment, RNA alkylation is quenched, i.e., stopped at the end the alkylation treatment.

Quenching the alkylation treatment can be carried out by technics well-known to the one skilled in the art.

In one embodiment, RNA alkylation quenching is carried out using a reducing agent.

Examples of suitable reducing agents include, but are not limited to, β-mercaptoethanol, dithiothreitol (DTT), tris(2-carboxyethyl)phosphine (TCEP), cysteine, N-acetyl cysteine, cysteamine, 2-mercaptoethanesulfonic acid sodium salt, dithioerythritol (DTE) and bis(2-mercaptoethyl)sulfone).

A non-limiting example of RNA alkylation quenching comprises adding to alkylated RNAs from about 1 mM final to about 100 mM final, preferably from about 10 mM final to about 50 mM final, preferably from about 10 mM final to about 30 mM final, preferably about 20 mM final of dithiothreitol (DTT).

Oxidative-nucleophilic-aromatic substitution of labelled RNAs can be carried out by technics well-known to the one skilled in the art. Such technics include, but are not limited to, those described in Schofield et al. (2018. *Nat Methods*. 15(3):221-225).

Preferably, oxidative-nucleophilic-aromatic substitution of labelled RNAs is carried out after extraction of RNAs as detailed hereinabove.

In one embodiment, labelled RNA oxidative-nucleophilic-aromatic substitution is carried out using an oxidant and a nucleophile.

Examples of suitable oxidants include, but are not limited to, sodium periodate ($NaIO_4$), meta-chloroperoxybenzoic acid (mCPBA), sodium iodate ($NaIO_3$) and hydrogen peroxide ($H_2O_2$).

In a preferred embodiment, the alkylating agent is sodium periodate ($NaIO_4$).

Examples of suitable nucleophiles include, but are not limited to, 2,2,2-trifluoroethanamine (TFEA), hydrazine, benzylamine, ammonia, methoxyamine, 1,1-dimethylethylenediaminen, aniline and 4-(trifluoromethyl)benzylamine.

In a preferred embodiment, the nucleophile is 2,2,2-trifluoroethanamine (TFEA).

Thiol-labelled RNAs being light-sensitive, in one embodiment, RNA oxidative-nucleophilic-aromatic substitution is carried out in the dark, or, at the very least, with protection from light.

In one embodiment, RNA oxidative-nucleophilic-aromatic substitution is not carried out in presence of a reducing agent.

In one embodiment, RNA oxidative-nucleophilic-aromatic substitution is quenched, i.e., stopped at the end the oxidative-nucleophilic-aromatic substitution treatment.

Quenching the oxidative-nucleophilic-aromatic substitution treatment can be carried out by technics well-known to the one skilled in the art.

Osmium-mediated transformation of labelled RNAs can be carried out by technics well-known to the one skilled in the art. Such technics include, but are not limited to, those described in Riml et al. (2017. *Angew Chem Int Ed Engl.* 56(43):13479-13483).

Preferably, osmium-mediated transformation of labelled RNAs is carried out after extraction of RNAs as detailed hereinabove.

In one embodiment, labelled RNA osmium-mediated transformation is carried out using osmium tetroxide ($OsO_4$) and ammonia.

Thiol-labelled RNAs being light-sensitive, in one embodiment, RNA oxidative-nucleophilic-aromatic substitution is carried out in the dark, or, at the very least, with protection from light.

In one embodiment, RNA osmium-mediated transformation is not carried out in presence of a reducing agent.

In one embodiment, RNA osmium-mediated transformation is quenched, i.e., stopped at the end the oxidative-nucleophilic-aromatic substitution treatment.

Quenching the osmium-mediated transformation treatment can be carried out by technics well-known to the one skilled in the art.

The generation of cDNA libraries, especially for sequencing purposes, is part of the knowledge of the one skilled in the art. Kits for cDNA library generation are commercially available, including, but not limited to, SMARTer Stranded Total RNA-Seq Kit (ClonTech), QuantSeq 3'mRNA-Seq Library Prep Kit (Lexogen), Nextera XT DNA Library Prep Kit (Illumina), TruSeq Nano DNA Library Prep Kit (Illumina), NEBNext DNA Library Prep Master Mix (New England Biolabs), NEBNext Ultra DNA Library Prep Kit (New England Biolabs) and JetSeq DNA Library Preparation Kit (Bioline).

In one embodiment, generating a cDNA library comprises some or all of the following sub-steps:

RNAs reverse-transcription, including:
first-strand cDNA synthesis (thereby obtaining a double-stranded mixed RNA-cDNA library),
optionally, RNA templates removal (thereby obtaining a single-stranded cDNA library),
second-strand cDNA synthesis (thereby obtaining a double-stranded cDNA library), and
optionally, double-stranded cDNA library purification.

Reverse-transcription of RNAs is carried out by technics well-known to the one skilled in the art, using a reverse-transcriptase enzyme and a mix of 4 deoxyribonucleotides triphosphate (dNTPs), namely deoxyadenosine triphosphate (dATP), deoxycytidine triphosphate (dCTP), deoxyguanosine triphosphate (dGTP) and (deoxy)thymidine triphosphate (dTTP).

In particular, methods for first-strand cDNA synthesis are well-known to the one skilled in the art. First-strand cDNA synthesis reactions can use a combination of sequence-specific primers, oligo(dT) or random primers. In one embodiment, the first-strand cDNA synthesis reaction uses oligo(dT) primers. In one embodiment, the first-strand cDNA synthesis reaction uses sequence-specific primers. In one embodiment, the first-strand cDNA synthesis reaction uses random primers.

In one embodiment, primers used for first-strand cDNA synthesis comprise a fixed nucleic acid sequence (comprising, e.g., adapters and/or indexes used for sequencing) and a priming nucleic acid sequence (complementary to the RNA template). In one embodiment, primers used for first-strand cDNA synthesis comprise a fixed 5'-end sequence and a priming 3'-end sequence. In one embodiment, primers used for first-strand cDNA synthesis comprise a fixed 3'-end sequence and a priming 5'-end sequence.

In particular, methods for RNA templates removal are well-known to the one skilled in the art. RNA template removal can be carried out, e.g., by incubating the double-stranded mixed RNA-cDNA library with RNase H.

RNAs reverse-transcription to generate a cDNA library can be carried out in a random manner, i.e., using random primers and thereby reverse-transcribing the whole or major part of the RNAs. Alternatively, RNAs reverse-transcription to generate a cDNA library can be carried out in a targeted manner, i.e., using specific primers and thereby creating a cDNA library of custom sequences only.

In one embodiment, generating a library of cDNA, in particular reverse-transcribing RNAs, leads to nucleotide substitution. Such nucleotide substitutions occur randomly in a small number on any reverse-transcribed RNA, in absence of chemical modification. However, an upsurge of such substitutions is observed during reverse-transcription of RNAs which were previously labelled, and further chemically-modified by techniques such as alkylation, oxidative-nucleophilic-aromatic substitution, osmium-mediated transformation or the like, as described hereinabove. This upsurge of substitutions is illustrated in the "Examples" section further below.

Amplifying the cDNA library can be carried out by methods well-known to the one skilled in the art.

Amplification of the cDNA library can be carried out in a random manner, i.e., using random primers and thereby amplifying the whole or major part of the cDNA library. Alternatively, amplification of the cDNA library can be carried out in a targeted manner, i.e., using specific primers and thereby amplifying only custom sequences in the cDNA library.

Sequencing the cDNA library can be carried out by methods well-known to the one skilled in the art. In one embodiment, sequencing the cDNA library is carried out by Next Generation Sequencing (NGS), deep sequencing or targeted sequencing of custom sequences.

Methods for NGS are known to the one skilled in the art, and comprise, but are not limited to, paired-end sequencing, sequencing by synthesis, single-read sequencing.

Platforms for NGS are available, and include, but are not limited to, Illumina MiSeq (Illumina), Ion Torrent PGM (ThermoFisher Scientific), PacBio RS (PacBio), Illumina GAIIx (Illumina), Illumina HiSeq 2000 (Illumina).

The step of sequencing the cDNA library can be carried out using commercially available kits, such as MiSeq reagent kit v2 (Illumina).

In one embodiment, sequencing the cDNA library yields a set of sequence reads.

In one embodiment, the method according to the present invention comprises a step of comparing the number of substituted nucleotides in the first set of sequence reads mapping against at least one microbial—preferably viral, bacterial, archaeal, fungal or protozoan—nucleic acid sequence hit with a control sequence.

By "substituted nucleotides", it is meant a nucleotide replaced by another with respect to the microbial—preferably viral, bacterial, archaeal, fungal or protozoan—nucleic acid sequence hit. Typically, any nucleotide can be replaced by any other nucleotide, such as a thymidine being replaced by a cytosine (T→C), by an adenine (T→A) or by a guanine (T→G). The same applies to adenine (A), cytosine (C) and guanine (G) being replaced by any of the three other nucleotides.

Such substitutions occur randomly in a small number, in particular during steps of reverse-transcription. The present invention is however based on the upsurge of such substitutions in the case where RNAs were previously labelled, and further submitted to chemical modification methods such as alkylation, oxidative-nucleophilic-aromatic substitution, osmium-mediated transformation and the like.

In one embodiment, the total number of substituted nucleotides in the first set of sequence reads mapping against the at least one microbial—preferably viral, bacterial, archaeal, fungal or protozoan—nucleic acid sequence hit is compared with the total number of substituted nucleotides in the control sequence.

In one embodiment, the number of T→C substitutions in the first set of sequence reads mapping against the at least one microbial—preferably viral, bacterial, archaeal, fungal or protozoan—nucleic acid sequence hit is compared to the number of T→C substitutions in the control sequence.

In one embodiment, the nucleotide substitution rates in the first set of sequence reads mapping against the at least one identified microbial—preferably viral, bacterial, archaeal, fungal or protozoan—nucleic acid sequence hit is compared to the nucleotide substitution rates in the control sequence.

In one embodiment, the T→C substitution rates in the first set of sequence reads mapping against the at least one microbial—preferably viral, bacterial, archaeal, fungal or protozoan—nucleic acid sequence hit is compared to the T→C substitution rates in the control sequence.

The "substitution rate", as used herein, is calculated as the number of one or several given nucleotide substitutions (e.g., T→C, or any other nucleotide substitution as defined hereinabove) divided by the total number of substitutions. Alternatively, the "substitution rate" may be calculated as the number of one or several given nucleotide substitutions divided by the total number of nucleotides in the sequence reads mapping against the at least one microbial—preferably viral, bacterial, archaeal, fungal or protozoan—nucleic acid sequence hit.

In one embodiment, the ratio of the T→C substitution rate between the sequence reads mapping against the at least one microbial—preferably viral, bacterial, archaeal, fungal or protozoan—nucleic acid sequence hit in the first set of sequence reads and in the control sequence, and the ratio of the average substitution rates of all other nucleotides (i.e., all but T→C) between the sequence reads mapping against the at least one microbial—preferably viral, bacterial, archaeal, fungal or protozoan—nucleic acid sequence hit in the first set of sequence reads and in the control sequence, are compared.

In one embodiment, the method comprises identifying at least one microbial—preferably viral, bacterial, archaeal, fungal or protozoan—nucleic acid sequence hit mapped against at least one sequence read.

In one embodiment, identification of at least one microbial—preferably viral, bacterial, archaeal, fungal or protozoan—nucleic acid sequence hit mapped against at least one sequence read comprises sub-steps of filtering the set of reads, assembling the sequence reads into contigs, aligning the sequence reads or contigs onto a database, identifying the at least one microbial—preferably viral, bacterial, archaeal, fungal or protozoan—nucleic acid sequence hit mapped against at least one sequence read or contig, and re-aligning the sequence reads or contigs onto the microbial—preferably viral, bacterial, archaeal, fungal or protozoan—nucleic acid sequence hit.

Filtering a set of sequence reads is part of the knowledge of the one skilled in the art.

In one embodiment, filtering a set of sequence reads may include, without limitation, suppressing sequence read duplicates, suppressing low quality sequence reads, suppressing sequence read homopolymers, removing fixed nucleic acid sequences from the sequence reads (such as, e.g., adapters and/or indexes used for sequencing), discarding endogenous sequence reads (i.e., sequence reads mapping a nucleic acid sequence belonging to the subject's cell), discarding unwanted sequence reads (such as, e.g., rRNA sequence reads and the like) and the like.

Such filtering can be carried out using software readily available to the one skilled in the art.

Assembling a set of sequence reads into contigs is part of the knowledge of the one skilled in the art.

Such assembly of sequence reads into contigs can be carried out using software readily available to the one skilled in the art.

Optionally, sequence reads or contigs may be translated into amino acid sequences.

Aligning a set of sequence reads or contigs is part of the knowledge of the one skilled in the art. Such alignment of sequence reads or contigs can be carried out using software readily available to the one skilled in the art.

In one embodiment, sequence reads or contigs are aligned on a microbial database, i.e., a database comprising microbial—preferably viral, bacterial, archaeal, fungal or protozoan—nucleic acid sequences or amino acid sequences (in the case where sequence reads or contigs were translated into amino acid sequences). Such database can be downloaded, e.g., from the EMBL Nucleotide Sequence Database.

Identifying at least one microbial—preferably viral, bacterial, archaeal, fungal or protozoan—nucleic acid sequence hit (or amino acid sequence hit in the case where sequence reads or contigs were translated into amino acid sequences) mapped against at least one sequence read or contig is part of the knowledge of the one skilled in the art.

Upon alignment of the set of sequence reads or contigs on a database, hit sequences from said database can be identified.

In one embodiment, at least one hit sequence is identified (and therefore selected) based on a threshold expected value (e-value) obtained upon alignment with the sequence reads or contigs. In one embodiment, a sequence hit is identified (and therefore selected) if the e-value obtained upon alignment of said sequence hit with at least one sequence read or contig is below $10^{-2}$, preferably below $5 \cdot 10^{-3}$, preferably below $10^{-3}$.

Re-aligning the sequence reads or contig onto the at least one microbial—preferably viral, bacterial, archaeal, fungal or protozoan—nucleic acid sequence hit (or amino acid sequence hit in the case where sequence reads or contigs were translated into amino acid sequences) previously identified (and therefore selected) is part of the knowledge of the one skilled in the art.

Such re-alignment of sequence reads or contigs can be carried out using software readily available to the one skilled in the art.

In one embodiment, upon re-alignment, at least one final consensus sequence of the at least one microbial—preferably viral, bacterial, archaeal, fungal or protozoan—nucleic acid sequence hit (or amino acid sequence hit in the case where sequence reads or contigs were translated into amino acid sequences) previously identified (and therefore selected) is determined.

In one embodiment, the control sequence is selected from:
- a second set of sequence reads mapping against said at least one microbial—preferably viral, bacterial, archaeal, fungal or protozoan—nucleic acid sequence hit, wherein the second set of sequence reads is obtained by sequencing a second set of RNAs obtained by culturing the sample, preferably the cell sample, in absence of an RNA-labelling agent;
- a second set of sequence reads mapping against said at least one microbial—preferably viral, bacterial, archaeal, fungal or protozoan—nucleic acid sequence hit, wherein the second set of sequence reads is obtained by sequencing a second set of RNAs obtained by culturing the sample, preferably the cell sample, in presence of an RNA-labelling agent but without submitting the extracted RNAs to conditions allowing for nucleotide substitution;
- a consensus microbial—preferably viral, bacterial, archaeal, fungal or protozoan—nucleic acid sequence, obtained from the sequence reads or contigs of the first set of sequence reads mapping against the at least one microbial—preferably viral, bacterial, archaeal, fungal or protozoan—nucleic acid sequence hit;
- a sequence corresponding to the same microbial—preferably viral, bacterial, archaeal, fungal or protozoan—nucleic acid sequence hit found in the closest microbial—preferably viral, bacterial, archaeal, fungal or protozoan—strain identified in nucleic acid sequence databases; and/or
- an analogous sequence corresponding to the same microbial—preferably viral, bacterial, archaeal, fungal or protozoan—nucleic acid sequence hit identified in nucleic acid sequence databases.

In one embodiment, the control sequence is a second set of sequence reads mapping against said at least one microbial—preferably viral, bacterial, archaeal, fungal or protozoan—nucleic acid sequence hit, wherein the second set of sequence reads is obtained by sequencing a second set of RNAs obtained by culturing the sample, preferably the cell sample, in absence of an RNA-labelling agent.

In this embodiment, the method according to the present invention comprises the steps of:
(a) sequencing a first and a second set of RNAs extracted from the sample, preferably the cell sample,
  wherein the first set of RNAs is obtained by culturing the sample, preferably the cell sample, in presence of an RNA-labelling agent and the second set of RNAs is obtained by culturing the sample, preferably the cell sample, in absence of an RNA-labelling agent,
  thereby obtaining a first and a second set of sequence reads,
(b) comparing the number of substituted nucleotides in the first set of sequence reads mapping against at least one microbial—preferably viral, bacterial, archaeal, fungal or protozoan—nucleic acid sequence hit with the number of substituted nucleotides in the second set of sequence reads mapping against said at least one microbial—preferably viral, bacterial, archaeal, fungal or protozoan—nucleic acid sequence hit, and
(c) concluding that the at least one microbial—preferably viral, bacterial, archaeal, fungal or protozoan—nucleic acid sequence hit belongs to a live microbe—preferably virus, bacterium, archaeon, fungus or protozoan—if the number of substituted nucleotides in the sequence reads mapping against the at least one microbial—preferably viral, bacterial, archaeal, fungal or protozoan—nucleic acid sequence hit in the first set of sequence reads is greater than in the second set of sequence reads.

Preferably, the first set of RNAs is obtained by culturing the sample, preferably the cell sample, in presence of an RNA-labelling agent, thereby obtaining labelled RNAs, and further submitting said labelled RNAs to nucleotide substitution as detailed hereinabove.

In one embodiment, the method according to the present invention comprises the steps of:
(a) sequencing a first and a second set of RNAs extracted from a sample, preferably a cell sample,
  wherein the first set of RNAs is obtained by culturing the sample, preferably the cell sample, in presence of an RNA-labelling agent and the second set of RNAs is obtained by culturing the sample, preferably the cell sample, in absence of an RNA-labelling agent,
  thereby obtaining a first and a second set of sequence reads,
(b) identifying at least one microbial—preferably viral, bacterial, archaeal, fungal or protozoan—nucleic acid sequence hit mapped against at least one sequence read of the first set of sequence reads,
(c) comparing the number of substituted nucleotides in the sequence reads mapping the at least one identified microbial—preferably viral, bacterial, archaeal, fungal or protozoan—nucleic acid sequence hit in the first and second set of sequence reads, and
(d) concluding that the at least one microbial—preferably viral, bacterial, archaeal, fungal or protozoan—nucleic acid sequence hit belongs to a live, active microbe—preferably virus, bacterium, archaeon, fungus or protozoan—if the number of substituted nucleotides in the sequence reads mapping the at least one identified microbial—preferably viral, bacterial, archaeal, fungal or protozoan—nucleic acid sequence hit in the first set of sequence reads is greater than in the second set of sequence reads.

In this embodiment, the method comprises a step of sequencing a first set of RNAs extracted from the sample, preferably the cell sample. In this embodiment, the sample, preferably the cell sample was cultured in presence of RNA-labelling agent.

In this embodiment, the step of sequencing a first set of RNAs extracted from the sample, preferably the cell sample, comprises one or more or all of the sub-steps of labelling RNAs, lysing the cells, extracting RNAs, substituting nucleotides in labelled RNAs, generating a cDNA library, amplifying the cDNA library and sequencing the cDNA library.

These sub-steps are defined and detailed hereinabove and apply to the sequencing of a first set of RNAs.

In this embodiment, the method comprises a further step of sequencing a second set of RNAs extracted from the sample, preferably the cell sample. In this embodiment, the sample, preferably the cell sample was cultured in absence of RNA-labelling agent.

In this embodiment, the step of sequencing a second set of RNAs extracted from the sample, preferably the cell sample, comprises one or more or all of the sub-steps of lysing the cells, extracting RNAs, generating a cDNA library, amplifying the cDNA library and sequencing the cDNA library.

These sub-steps are defined and detailed hereinabove and apply to the sequencing of a second set of RNAs.

In one embodiment, the control sequence is a second set of sequence reads mapping against said at least one microbial—preferably viral, bacterial, archaeal, fungal or protozoan—nucleic acid sequence hit, wherein the second set of sequence reads is obtained by sequencing a second set of RNAs obtained by culturing the sample, preferably the cell sample, in presence of an RNA-labelling agent but without submitting the extracted RNAs to conditions allowing for nucleotide substitution.

In this embodiment, the method according to the present invention comprises the steps of:
(a) sequencing a first and a second set of RNAs extracted from the sample, preferably the cell sample,
    wherein the first and the second set of RNAs are obtained by culturing the sample, preferably the cell sample, in presence of an RNA-labelling agent, thereby obtaining labelled RNAs, and
    wherein the first set of RNAs is obtained from a first fraction of the labelled RNAs which is submitted to nucleotide substitution, and the second set of RNAs is obtained from a second fraction of the labelled RNAs which is not submitted to nucleotide substitution,
    thereby obtaining a first and a second set of sequence reads,
(b) comparing the number of substituted nucleotides in the first set of sequence reads mapping against at least one microbial—preferably viral, bacterial, archaeal, fungal or protozoan—nucleic acid sequence hit with the number of substituted nucleotides in the second set of sequence reads mapping against said at least one microbial—preferably viral, bacterial, archaeal, fungal or protozoan—nucleic acid sequence hit, and
(c) concluding that the at least one microbial—preferably viral, bacterial, archaeal, fungal or protozoan—nucleic acid sequence hit belongs to a live microbe—preferably virus, bacterium, archaeon, fungus or protozoan—if the number of substituted nucleotides in the sequence reads mapping against the at least one microbial—preferably viral, bacterial, archaeal, fungal or protozoan—nucleic acid sequence hit in the first set of sequence reads is greater than in the second set of sequence reads.

In one embodiment, the control sequence may be a consensus microbial—preferably viral, bacterial, archaeal, fungal or protozoan—nucleic acid sequence. In one embodiment, a consensus microbial—preferably viral, bacterial, archaeal, fungal or protozoan—nucleic acid sequence may be obtained from multiple sequence reads of the first set of sequence reads mapping against the at least one microbial—preferably viral, bacterial, archaeal, fungal or protozoan—nucleic acid sequence hit. Such a consensus sequence can be readily determined since it has been observed that not all targeted nucleotides are thio-labelled and/or substituted upon nucleotide substitution procedure. Indeed, a sufficient number of targeted nucleotides is substituted to allow discrimination according to the method of the present invention; but this number remains sufficiently low to establish a consensus sequence.

In one embodiment, the control sequence may be a nucleic acid sequence corresponding to the same microbial—preferably viral, bacterial, archaeal, fungal or protozoan—nucleic acid sequence hit, but found in the closest microbial—preferably viral, bacterial, archaeal, fungal or protozoan—strain identified in nucleic acid sequence databases.

In one embodiment, the control sequence may be an analogous sequence corresponding to the same microbial—preferably viral, bacterial, archaeal, fungal or protozoan—nucleic acid sequence hit identified in nucleic acid sequence databases.

In one embodiment, the method according to the present invention comprises a step of concluding if the at least one microbial—preferably viral, bacterial, archaeal, fungal or protozoan—nucleic acid sequence hit belongs to a live microbe—preferably virus, bacterium, archaeon, fungus or protozoan—.

In one embodiment, the live microbe—preferably virus, bacterium, archaeon, fungus or protozoan—is characterized by taxonomic assignment of the at least one microbial—preferably viral, bacterial, archaeal, fungal or protozoan—nucleic acid sequence hit.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the total number of nucleotide substitutions in the sequence reads mapping against the at least one microbial—preferably viral, bacterial, archaeal, fungal or protozoan—nucleic acid sequence hit in the first set of sequence reads is greater than the total number of nucleotide substitutions in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the number of T→C substitutions in the sequence reads mapping against the at least one microbial—preferably viral, bacterial, archaeal, fungal or protozoan—nucleic acid sequence hit in the first set of sequence reads is greater than the number of T→C substitutions in the control sequence.

In one embodiment, "the [ . . . ] number of [ . . . ] substitutions [ . . . ] in the first set of sequence reads is greater than the [ . . . ] number of [ . . . ] substitutions [ . . . ] in the control sequence" when the number of substitutions is twice greater, preferably three times greater, more preferably 4, 5, 6, 7, 8, 9, 10, 15, 20, 50, 100 times greater in the sequence reads mapping against the at least one microbial—preferably viral, bacterial, archaeal, fungal or protozoan—nucleic acid sequence hit in the first set of sequence reads than in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the nucleotide substitution rate in the sequence reads mapping against the at least one microbial—preferably viral, bacterial, archaeal, fungal or protozoan—nucleic acid sequence hit in the first set of sequence reads is greater than the nucleotide substitution rate in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the T→C substitution rate in the sequence reads mapping against the at least one microbial—preferably viral, bacterial, archaeal, fungal or protozoan—nucleic acid sequence hit in the first set of sequence reads is greater than the T→C substitution rate in the control sequence.

As used herein, the term "T→C substitution rate" may be defined with the following formula:

$$T \to C \text{ substitution rate} = \frac{\text{Number of } C \text{ nucleotides identified when a } T \text{ was expected}}{\text{Total number of expected } T}$$

In one embodiment, "the [ . . . ] substitution rate [ . . . ] in the first set of sequence reads is greater than the [ . . . ] substitution rate [ . . . ] in the control sequence" when the substitution rate is twice greater, preferably three times greater, more preferably 4, 5, 6, 7, 8, 9, 10, 15, 20, 50, 100 times greater in the sequence reads mapping against the at least one microbial—preferably viral, bacterial, archaeal, fungal or protozoan—nucleic acid sequence hit in the first set of sequence reads than in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the T→C substitution rate is greater than the average substitution rates of all other nucleotides in the sequence reads mapping against the at least one microbial—preferably viral, bacterial, archaeal, fungal or protozoan—nucleic acid sequence hit in the first set of sequence reads.

In one embodiment, "the T→C substitution rate is greater than the average substitution rates of all other nucleotides" when the T→C substitution rate is twice greater, preferably three times greater, more preferably 4, 5, 6, 7, 8, 9, 10, 15, 20, 50, 100 times greater than the average substitution rates of all other nucleotides.

By "average substitution rates of all other nucleotides", it is meant the average of A→C, A→G, A→T, C→A, C→G, C→T, T→A, T→G, G→A, G→C and G→T substitution rates.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the T→C substitution rate is greater than the average substitution rates of T→A and T→G in the sequence reads mapping against the at least one microbial—preferably viral, bacterial, archaeal, fungal or protozoan—nucleic acid sequence hit in the first set of sequence reads.

In one embodiment, "the T→C substitution rate is greater than the average substitution rates of T→A and T→G" when the T→C substitution rate is twice greater, preferably three times greater, more preferably 4, 5, 6, 7, 8, 9, 10, 15, 20, 50, 100 times greater than the average substitution rates of T→A and T→G. In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the ratio of the T→C substitution rate between the sequence reads mapping against the at least one microbial—preferably viral, bacterial, archaeal, fungal or protozoan—nucleic acid sequence hit in the first set of sequence reads and in the control sequence is greater than the ratio of the average substitution rates of all other nucleotides between the sequence reads mapping against the at least one microbial—preferably viral, bacterial, archaeal, fungal or protozoan—nucleic acid sequence hit in the first set of sequence reads and in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the ratio of the T→C substitution rate between the sequence reads mapping against the at least one microbial—preferably viral, bacterial, archaeal, fungal or protozoan—nucleic acid sequence hit in the first set of sequence reads and in the control sequence is greater than the ratio of the average substitution rates of T→A and T→G between the sequence reads mapping against the at least one microbial—preferably viral, bacterial, archaeal, fungal or protozoan—nucleic acid sequence hit in the first set of sequence reads and in the control sequence.

In one embodiment, it is concluded that the at least one microbial—preferably viral, bacterial, archaeal, fungal or protozoan—nucleic acid sequence hit belongs to a live microbe—preferably virus, bacterium, archaeon, fungus or protozoan—if the T→C substitution index in the sequence reads mapping against the at least one microbial—preferably viral, bacterial, archaeal, fungal or protozoan—nucleic acid sequence hit in the first set of sequence reads is greater than a threshold value. In this embodiment, the threshold value can be determined experimentally. In one embodiment, the threshold value is greater than the T→C substitution index in the sequence reads mapping against the at least one microbial—preferably viral, bacterial, archaeal, fungal or protozoan—nucleic acid sequence hit in the second set of sequence reads. In one embodiment, the threshold value is at least 2, preferably at least 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 or more.

As used herein, the term "T→C substitution index" may be defined with the following formula:

$$T \to C \text{ substitution index} = \frac{\text{``}T \to C\text{'' rate}}{\text{Mean (``}T \to A\text{'', ``}T \to G\text{'' rates)}}$$

The methods for discriminating between live and dead microbes—preferably viruses, bacteria, archaea, fungi or protozoans—in a sample, preferably a cell sample, comprising discriminating between transcriptionally-active and inert microbial—preferably viral, bacterial, archaeal, fungal or protozoan—nucleic acid sequences in the sample, preferably the cell sample, according to the present invention, are useful in a number of different applications.

Indeed, the risk of microbial, in particular viral, bacterial, archaeal, fungal or protozoan, contamination is a topic of major concern for biological products. This includes both the risk of contamination of Good Manufacturing Practice (GMP) facilities and the final drug product. Virus testing of raw materials, cells, virus seeds, master/working banks, serum batches for vaccines, etc. is key for the safety of the drug product. This is particularly critical for live vaccines, gene therapy viral vectors and cell therapy drug products since their production do not include downstream viral elimination steps. As a result, the safety of these products heavily relies on viral testing during the production process.

All previously reported contaminations of products based on cell cultures have been due to unpredictable animal viruses that were not identified during viral testing of raw materials or production cells. In fact, classical viral testing is limited since many viruses do not grow in cell lines used for in vitro tests or in rodents or eggs used for in vivo tests.

The methods of the present invention offer an alternative approach to accurately test samples for contamination and to distinguish between live—including latent—microbes; and harmless contamination of inert microbial nucleic acids fragments (e.g., fragmented nucleic acids of microbes after gamma-irradiation inactivation).

Based on this, numerous industrial applications are foreseeable.

In the field of vaccines, the control of inactivated vaccines is typically carried out nowadays by cultivating the vaccine which is deemed to be inactivated, then seek for the presence of active microbes. The methods of the present invention would allow to differentiate live microbes from the background noise of inert microbial nucleic acid sequence which are inactivated and thus harmless.

Similarly, the methods according to the present invention can be readily implemented to detect contamination with live microbes in biological samples, such as raw material (e.g., serum batches in the case of vaccines), cells, master/working banks, etc. but also in blood cultures and other types of biological samples used for diagnosis. After antibiotic treatment in a subject for example, it could be considered to test the subject for the presence or absence of remaining live microbes, and thereby identify potential treatment-resistant microbes.

In the field of virotherapy, the methods according to the present invention can be implemented to test for the presence or absence of replicative revertant viruses in viral vectors, such as those used in, e.g., gene therapy.

Preservation medium can also be subjected to microbial contamination, and the methods according to the present invention may readily be used to test for such contamination before contacting the sample to preserve.

The field of possibilities also extends to non-biological samples. For example, food safety is a major concern. Sanitary scandals and the emergence of a food demand focused on quality and safety resonates with the food testing in search of microbial contamination.

The methods of the present invention can solve this issue by providing a practical and definite answer as to whether a food sample is contaminated by live microbes or not.

Environmental samples may also be tested. For example, water and/or air-conditioning circuits are known to potentially carry microbes. The methods according to the present invention can be implemented to confirm the presence or absence of such live microbes.

Another object of the present invention is a diagnosis method, preferably an in vitro diagnosis method, of a microbial—preferably viral, bacterial, archaeal, fungal or protozoan—infection in a subject.

In one embodiment, the diagnosis method according to the present invention comprises a step of providing a sample, preferably a cell sample, from the subject.

In one embodiment, the diagnosis method according to the present invention further comprises a step of performing any of the methods for discriminating between transcriptionally-active and inert microbial—preferably viral, bacterial, archaeal, fungal or protozoan—nucleic acid sequences in a sample, preferably a cell sample, according to the present invention.

In one embodiment, the diagnosis method according to the present invention further comprises a step of diagnosing the subject as having a microbial—preferably viral, bacterial, archaeal, fungal or protozoan—infection if the at least one identified microbial—preferably viral, bacterial, archaeal, fungal or protozoan—nucleic acid sequence hit belongs to a live microbe—preferably virus, bacterium, archaeon, fungus or protozoan.

Another object of the present invention is a method of treating a microbial—preferably viral, bacterial, archaeal, fungal or protozoan—infection in a subject.

In one embodiment, the method of treating a microbial infection according to the present invention comprises a step of carrying the diagnosis method according to the present invention; and a step of treating the subject if said subject was diagnosed as having a microbial—preferably viral, bacterial, archaeal, fungal or protozoan—infection.

Means and methods of treating a microbial infection are well known to the one skilled in the art, and include, without limitation, the administration of at least one antiviral, antibacterial, antifungal or antiprotozoal agent to the subject.

Suitable examples of antiviral agents include, without limitation, those classified in the therapeutic subgroup J05 of the Anatomical Therapeutic Chemical Classification System. Further examples include, but are not limited to, acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, zinc salts, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH—C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, zinviroxime, and combinations thereof.

Suitable examples of antibacterial agents include, without limitation, those classified in the therapeutic subgroup J01 of the Anatomical Therapeutic Chemical Classification System. Further examples include, but are not limited to, aminoglycosides (such as, e.g., amikacin, gentamicin, kanamycin, neomycin, netilmicin, streptomycin, tobramycin, paromycin, and the like), ansamycins (such as, e.g., geldanamycin, herbimycin and the like), carbacephems (such as, e.g., loracarbef and the like), carbapenems (such as, e.g., ertapenum, doripenem, imipenem, cilastatin, meropenem, and the like), first generation cephalosporins (such as, e.g., cefadroxil, cefazolin, cefalotin, cephalexin, and the like), second generation cephalosporins (such as, e.g., ceflaclor, cefamandole, cefoxitin, cefprozil, cefuroxime, and the like), third generation cephalosporins (such as, e.g., cefixime, cefdinir, cefditoren, cefoperazone, cefotaxime, cefpodoxime, ceftazidime, ceftibuten, ceftizoxime, ceftriaxone, and the like), fourth generation cephalosporins (such as, e.g., cefepime and the like), fifth generation cephalosporins (such as, e.g., ceftobiprole, and the like), glycopeptides (such as, e.g., teicoplanin, vancomycin, and the like), macrolides (such as, e.g., axithromycin, clarithromycin, dirithromycine, erythromycin, roxithromycin, troleandomycin, telithromycin, spectinomycin, and the like), monobactams (such as, e.g., axtreonam, and the like), penicilins (such as, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, and the like), antibiotic polypeptides (such as, e.g., bacitracin, colistin, polymyxin B, and the like), quinolones (such as, e.g., ciprofloxacin, enoxacin, gatifloxacin, levofloxacin, lemefloxacin, moxifloxacin, norfloxacin, orfloxacin, trovafloxacin, and the like), sulfonamides (such as, e.g., mafenide, prontosil, sulfacetamide, sulfamethizole, sulfanilamide, sulfasalazine, sulfisoxazole, trimethoprim, trimethoprim-sulfamethoxazole, and the like), tetracyclines (such as, e.g., demeclocycline, doxycycline, minocycline, oxytetracycline, tetracycline, and the like), other antibiotics (such as, e.g., arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, and the like), and combinations thereof.

Suitable examples of antifungal agents include, without limitation, those classified in the therapeutic subgroup J02 of the Anatomical Therapeutic Chemical Classification System. Further examples include, but are not limited to, abafungin, albaconazole, amorolfine, amphotericin B, anidulafungin, atovaquone, biafungin, bifonazole, bromochlorosalicylanilide, butenafine, butoconazole, caspofungin, chlormidazole, chlorophetanol, chlorphenesin, ciclopirox, cilofungin, citronella oil, clotrimazole, croconazole, crystal violet, dapsone, dimazole, eberconazole, econazole, efinaconazole, ethylparaben, fenticonazole, fluconazole, flucytosine, flutrimazole, fosfluconazole, griseofulvin, haloprogin, hamycin, hexaconazole, isavuconazole, isoconazole, itraconazole, ketoconazole, lemon grass, lemon myrtle, luliconazole, micafungin, miconazole, naftifine, natamycin, neticonazole, nystatin, omoconazole, orange oil, oxiconazole, patchouli, pentamidine, polynoxylin, posaconazole, potassium iodide, ravuconazole, salicylic acid, selenium disulfide, sertaconazole, sodium thiosulfate, sulbentine, sulconazole, taurolidine, tavaborole, tea tree oil, terbinafine, terconazole, ticlatone, tioconazole, tolciclate, tolnaftate, tribromometacresol, undecylenic acid, voriconazole, Whitfield's ointment, and combinations thereof.

Suitable examples of antiprotozoal agents include, without limitation, those classified in the therapeutic subgroup P01 of the Anatomical Therapeutic Chemical Classification System. Further examples include, but are not limited to, albendazole, amodiaquine, amphotericin B, arsthinol, artemether, artemisinin, artemotil, arterolane, artesunate, atovaquone, azanidazole, benznidazole, broxyquinoline, carnidazole, chiniofon, chlorhexidine, chloroquine, chlorproguanil, chlorquinaldol, clefamide, clindamycin, clioquinol, dehydroemetine, difetarsone, dihydroartemisinin, diiodohydroxyquinoline, diloxanide, doxycycline, eflornithine, emetine, etofamide, fexinidazole, fumagillin, furazolidone, glycobiarsol, halofantrine, hydroxychloroquine, iodoquinol, lumefantrine, mefloquine, meglumine antimoniate, melarsoprol, mepacrine, metronidazole, miltefosine, nifurtimox, nimorazole, nitazoxanide, ornidazole, pamaquine, paromomycin, pentamide, phanquinone, piperaquine, primaquine, proguanil, propamidine, propenidazole, pyrimethamine, pyronaridine, quinacrine, quinidine, quinine, secnidazole, sodium stibogluconate, sulfadiazine, sulfadoxine, sulfalene, sulfamethoxazole, suramin, tafenoquine, teclozan, tenonitrozole, tetracycline, tilbroquinol, tinidazole, trimethoprim, trimetrexate, and combinations thereof.

Another object of the present invention is a method for assessing the risk of microbial—preferably viral, bacterial, archaeal, fungal or protozoan—contamination in a sample.

In one embodiment, the method for assessing the risk of microbial—preferably viral, bacterial, archaeal, fungal or protozoan—contamination according to the present invention comprises a step of providing a sample. In one embodiment, the sample by be a biological sample or a non-biological sample.

In one embodiment, the method for assessing the risk of microbial—preferably viral, bacterial, archaeal, fungal or protozoan—contamination according to the present invention comprises a step of performing any of the methods for discriminating between transcriptionally-active and inert microbial—preferably viral, bacterial, archaeal, fungal or protozoan—nucleic acid sequences in a sample according to the present invention.

In one embodiment, the method for assessing the risk of microbial—preferably viral, bacterial, archaeal, fungal or protozoan—contamination according to the present invention comprises a step of concluding that the sample is at risk of being contaminated if the at least one identified microbial—preferably viral, bacterial, archaeal, fungal or protozoan—nucleic acid sequence hit belongs to a live microbe—preferably virus, bacterium, archaeon, fungus or protozoan.

EXAMPLES

The above and other aspects and features of the present invention will be further illustrated by the following examples. These examples are illustrative only and not intended to be limiting.

Example 1: Detection of Replicating Tick-Borne Encephalitis Virus (TBEV) in Cultured Vero Cells Materials and Methods
Material
Vero cells were grown in minimum essential medium (MEM) supplemented with 2% fetal bovine serum (FBS). The virus used for infection is the Tick-Borne Encephalitis Virus (TBEV), a member of the family Flaviviridae, consisting of a ssRNA(+) genome with an average size of 10 kb.
Methods
Virus Infection
Vero cells were plated at 400 000 cells/well in 3 wells of a MW6 plate, in order to reach $10^6$ cells/well after 24 hours.
Cells were then infected with the TBEV at a MOI (multiplicity of infection) of 1 and incubated 1 hour on ice with agitation.
For one well, the medium was removed just after the incubation and the cells were lysed with 1 mL of TRIzol and stored at −80° C. until RNA extraction (Condition 1).
For the two other wells (Conditions 2 and 3), the medium was removed and replaced by MEM+2% FBS and incubated overnight at 37° C.
4sU Labelling
This step was performed using the SLAMseq Kinetic kit—Anabolic Kinetics Module (Lexogen, Cat. No. 061).
Incorporation of 4-thiouridine (4sU) in the cell culture medium during the cell culture allows 4sU nucleotides to be incorporated into newly synthesized RNA.

The media containing 800 μM 4sU was prepared by adding 8 μL of 100 nM 4sU in 992 μL of MEM.

The day following the viral infection, the medium was removed and replaced by medium without 4sU in one well (Condition 2) or 4sU-containing medium (800 μM) for the last well (Conditions 3). Six hours later, the medium was removed and replaced by fresh medium without 4sU in Condition 2, or by fresh 4sU-containing medium (800 μM) in Condition 3.

Three hours later, the medium was removed from the three wells, and the cells were lysed with 1 mL of TRIzol and stored à–80° C. until RNA extraction.

RNA Sampling

This step was performed using the SLAMseq Kinetic kit—Anabolic Kinetics Module (Lexogen, Cat. No. 061).

The RNA extraction was performed in the dark and using a chloroform:isoamyl alcohol mix 24:1 (Sigma Aldrich, Cat. No. 25666) followed by isopropanol/ethanol precipitation. During extraction, reducing agent (RA) was used to maintain the 4sU-treated samples under reducing conditions.

The isolated total RNA contains both existing (unlabeled) and newly synthesized (labeled) RNA.

Alkylation

This step was performed using the SLAMseq Kinetic kit—Anabolic Kinetics Module (Lexogen, Cat. No. 061).

Total extracted RNA of Condition 3 was mixed with iodoacetamide (IAA), which modifies the 4-thiol group of 4sU-containing nucleotides via the addition of a carboxyamidomethyl group. The RNA was then purified using ethanol precipitation prior to proceeding to library preparation.

Library Preparation

The SMARTer Stranded Total RNA-Seq Kit—Pico Input Mammalian (ClonTech) was used for a direct construction of libraries starting with 10 ng of RNA. The workflow used in this kit incorporates a proprietary technology (PathoQuest, Paris, France) that depletes ribosomal cDNA using probes specific to mammalian rRNA and some mitochondrial RNA.

Sequencing

Sequencing was performed on the NextSeq instrument (Illumina) using the NextSeq 500/550 High Output kit v2 (FC-404-2002, Illumina).

Sequencing was single-read with a read length of 150 nucleotides and approximatively 125 million of reads per sample were generated.

Outline

Table 1 bellow summarize the protocol used for the three different Conditions (1, 2 and 3).

TABLE 1

| outline of the protocol | | | |
|---|---|---|---|
| | Condition 1 | Condition 2 | Condition 3 |
| Step 1 | TBEV infection | TBEV infection | TBEV infection |
| Step 2 | RNA Extraction (day 0) | RNA extraction (day 1) | 4sU labelling |
| Step 3 | Library preparation | Library preparation | RNA extraction (day 1) |
| Step 4 | Sequencing | Sequencing | Alkylation |

TABLE 1-continued

| outline of the protocol | | | |
|---|---|---|---|
| | Condition 1 | Condition 2 | Condition 3 |
| Step 5 | — | — | Library preparation |
| Step 6 | — | — | Sequencing |

Bioinformatic Analysis—TBEV Genome Analysis

The first objective of this study was to obtain a complete TBEV genome sequence of this isolate to be used as a reference. This analysis was performed on the infected sample at day 0, without 4sU treatment.

Raw Reads Filtering

First, the raw data reads were filtered to select high-quality and relevant reads.

Raw data were sorted out to suppress or cut the duplicates, low quality reads and homopolymers (proprietary software). Sequences introduced during Illumina® libraries preparation (adapters, primers) were removed with Skewer (Jiang et al., 2014. BMC Bioinformatics. 15:182).

Finally, endogenous primate reads (from Vero cells) aligned to the human genome (Reference GRCh37/hg19) or reads aligned to bacterial rRNA were discarded.

Local alignments were performed with BWA (Li et al., 2009. Bioinformatics. 25(14):1754-60).

Human genome was downloaded from the UCSC Genome Browser (2002. Genome Res. 12(6):996-1006). Bacterial rRNA database was downloaded from the EMBL-EBI ENA rRNA database, with additional in-house sequences cleaning and clustering process.

These filtered reads were considered as sequences of interest.

De Novo Assembly

The set of remaining and relevant reads was then assembled into longer sequences named contigs. This de novo assembly step was performed with CLC assembly cell solution (Qiagen).

Agnostic Virus Identification

Resulting contigs and non-assembled reads (singletons) were aligned using BLAST alignment (Altschul et al., 1990. J Mol Biol. 215(3):403-10) on viral and comprehensive databases. Contigs and singletons were first aligned on a viral nucleotide database. Hits with a e-value below $10^{-3}$ were aligned on a comprehensive nucleotide database. If their best hit was still a viral taxonomy, hits were reported.

Nucleotide viral and comprehensive databases were downloaded on November 2017 from the EMBL-EBI nucleotide sequence database STD. A proprietary software was developed to remove duplication and low confidence sequences (because too short, multiple taxonomies, low-quality associated keywords, etc.).

The contigs without any viral nucleotide hit were similarly aligned successively on viral and comprehensive protein databases to check for more distant viral hits.

Protein viral and comprehensive databases were downloaded on November 2017 from the Uniref100 database. The Uniref100 database is already non-redundant but a taxonomic cleaning process was performed to produce the final databases.

The taxonomic assignment reported the best hit results. Contigs not assigned after these two rounds of alignment were classified as unknown or non-viral species.

Table 2 below shows the results of the analysis.

TABLE 2

| agnostic viruses identification | | | |
|---|---|---|---|
| | Condition 1 | Condition 2 | Condition 3 |
| Total reads | 153379022 | 153360490 | 149549706 |
| FILTERING | | | |
| Duplicates/Quality | 84575371 | 85885045 | 73631007 |
| Adapters | 84575497 | 85884068 | 73629933 |
| Host | 19348675 | 21678833 | 27726895 |
| rRNA | 19314195 | 21637189 | 27664792 |
| ASSEMBLY | | | |
| Contigs | 32777 | 246669 | 460995 |
| Singletons | 2800174 | 2937361 | 3951554 |
| % assembled reads | 85.50% | 86.42% | 85.72% |
| TBEV RESULTS | | | |
| Nb contigs | 4 | 127 | 143 |
| Nb reads in contigs | 100031 | 2514666 | 2255875 |
| Nb singletons | 145 | 5052 | 3932 |
| Total reads | 100176 | 2519718 | 2259807 |
| Average contigs identity (%) | 91.23% | 92.06% | 91.71% |
| ADDITIONNAL CLOSE SPECIES (TOTAL READS) | | | |
| Machupo mammarenavirus | 1 | 2 | |
| Louping ill virus | | 14 | |
| Bovine viral diarrhea virus 1 | 12 | 7 | 9 |
| Bovine viral diarrhea virus 2 | | 1 | |
| Bovine viral diarrhea virus 3 | | 1 | |
| Singapore grouper iridovirus | 48 | | 41 |
| Rotavirus C | 1 | | |
| Cercopithecine betaherpesvirus 5 | | 25 | |
| Stealth virus 5 | | | 1 |
| Human gammaherpescirus 8 | | 23 | 6 |
| uncultured virus | | | 30 |
| Simian retrovirus | | 3 | 17 |
| Squirrel monkey retrovirus | 923291 | 837907 | 1064215 |
| Primate T-lymphotropic virus 1 | 5 | 29 | 10 |
| Baboon endogenous virus | 8503 | 8691 | 7710 |
| Feline leukemia virus | 2 | | 3 |
| Human endogenous retrovirus | 478 | 280 | 529 |
| Human endogenous retrovirus K | 16 | 35 | 37 |
| Human endogenous retrovirus W | 64 | 53 | 37 |
| Retroviridae (no genus, no species) | | | 4 |

TBEV Final Consensus Edition

This process identified a contig encompassing the full TBEV genome sequence.

All the reads were then realigned with CLC assembly cell solution (Qiagen) on this sequence to extract a final consensus sequence. This sequence was labeled "TBEV REFERENCE" for the study.

Bioinformatic Analysis—Nucleotides Substitution Rate Study

The objective was to compare the reads from the different samples to check if the "T-to-C" substitution rate was significantly higher in the 4sU+alkylation sample (Condition 3).

Tick Borne Encephalitis Virus Bank Creation

The "TBEV REFERENCE" sequence was used to create a blast bank.

In order to detect potential sequences with a very high "T-to-C" substitution rate, the reference sequence was also modified by substituting every T by a C. This sequence was named "TBEV T-C REFERENCE". The "TBEV REFERENCE" and "TBEV T-C REFERENCE" sequences were merged together to form a single "TBEV BLAST" bank.

Raw Reads Filtering

First, a quality filtering process was performed to remove or trim low-quality reads (proprietary software).

Then sequences introduced during Illumina libraries preparation (adapters, primers) were removed with Skewer (Jiang et al., 2014. *BMC Bioinformatics*. 15:182).

To avoid any analysis bias, duplicated reads were not removed.

Filtered Reads Blast on TBEV Blast Bank

The set of remaining and relevant reads was then aligned by BLAST (Altschul et al., 1990. *J Mol Biol*. 215(3):403-10) on the previously designed "TBEV BLAST" bank. The maximal e-value was set to $10^{-8}$.

All aligned reads were considered as TBEV positive and selected for the next step of the analysis.

Mapping of Selected Reads on TBEV Complete Genome

TBEV-positive reads were then realigned by mapping with CLC assembly cell solution (Qiagen) on the "TBEV REFERENCE" sequence. A quality control was set to ensure that at least 99% of the blast-selected reads were positively realigned on the reference.

Table 3 below summarizes the number of mapped sense and antisense reads obtained for each condition and the resulting coverage of the sequence.

TABLE 3 reads mapping, orientation and coverage.

|  | Number of reads | Coverage (%) |
|---|---|---|
| Condition 1 | | |
| Total | 160085 | 100.00 |
| Sens | 159647 | 100.00 |
| Antisens | 438 | 45.48 |
| % of antisens reads | 0.27 | |
| Condition 2 | | |
| Total | 6408291 | 100.00 |
| Sens | 6385645 | 100.00 |
| Antisens | 22646 | 99.06 |
| % of antisens reads | 0.353 | |
| Condition 3 | | |
| Total | 5240211 | 100.00 |
| Sens | 5221070 | 100.00 |
| Antisens | 19141 | 95.95 |
| % of antisens reads | 0.365 | |

Substitutions Rate Estimation

The CLC program "cic_find_variations" was used to detect every mismatch at every position of the TBEV study reference. The global variations profile was then analyzed by a proprietary script to define each nucleotide substitution rate. The proportion of substituted nucleotides was compared to the total number of aligned nucleotides. Typically, the "T-to-C" substitution rate is calculated using the following formula:

$$\frac{\text{Number of } C \text{ nucleotides identified when a } T \text{ was expected}}{\text{Total number of aligned nucleotides}}$$

TBEV Stranded Analysis

A targeted and stranded analysis was performed on the TBEV identified reads. This analysis performs a more stringent mapping alignment of filtered reads. This alignment provides a detailed horizontal genome coverage and depth profile.

Local alignments were performed with BWA (Li et al., 2009. *Bioinformatics*. 25(14):1754-60).

Since the samples' libraries were prepared using the SMARTer Stranded RNA-Seq Kit, the RNA strand information was retained. Therefore, a mapping alignment analysis provided information on the mother strand of each read (sense or reverse relative to the mother strand).

The transcripts coverage allowed to conclude on the viral replication signature in the cell sample.

Results and Conclusion

The ratio of the "T-to-C" substitution rate calculated on the mismatches mapped on the TBEV reference genome in Condition 3 over the T-to-C substitution rate calculated on the mismatches mapped on the TBEV reference genome in Condition 1 is equal to 7.86:1 (Table 4).

This indicates an increase of the proportion of TBEV RNA species having incorporated 4sU, hence the neo-synthesis of viral RNA during the 9 hours incubation of the Vero cell culture in medium containing 4sU.

The method exemplified here allows thus the detection of replicating the (+)ssRNA virus, TBEV, using metabolic labelling.

TABLE 4

T-to-C substitution rate.

|  | Condition 1 | Condition 2 | Condition 3 |
|---|---|---|---|
| Total mapped nt | 22613213 | 906722034 | 731556753 |
| Total mismatchs | 64625 | 2551959 | 3131703 |
| Mismatch rate | 0.29% | 0.28% | 0.43% |
| Number of T→C substitutions | 4751 | 189637 | 1209349 |
| Number of T→C substitutions/ Total mismatchs | 7.35% | 7.43% | 38.62% |
| Number of T–>C substitutions/ Total mapped nt | 0.02% | 0.02% | 0.17% |
| Other nt substitution rates/ Total mapped nt | | | |
| A→C | 0.03% | 0.03% | 0.02% |
| A→G | 0.02% | 0.02% | 0.02% |
| A→T | 0.02% | 0.02% | 0.01% |
| C→A | 0.05% | 0.04% | 0.04% |
| C→G | 0.01% | 0.01% | 0.01% |
| C→T | 0.02% | 0.02% | 0.03% |
| T→A | 0.03% | 0.03% | 0.03% |
| T→G | 0.02% | 0.02% | 0.02% |
| G→A | 0.03% | 0.03% | 0.03% |
| G→C | 0.03% | 0.03% | 0.03% |
| G→T | 0.02% | 0.02% | 0.02% |
| Minimum | 0.01% | 0.01% | 0.01% |
| Maximum | 0.05% | 0.04% | 0.04% |
| Average | 0.02% | 0.02% | 0.02% |

Example 2: Detection of Replicating Squirrel Monkey Retrovirus (SMRV) in Cultured Vero Cells Following agnostic virus identification in Example 1, the best hit results showed contigs assigned to the Squirrel Monkey Retrovirus. This virus is known to be endogenous and fully integrated in some monkey species. In particular, Vero cells used in this study have been described to harbors a variety of simian endogenous type D retrovirus sequences, in particular SMRV sequences (Sakuma et al., 2018. *Sci Rep*. 8(1):644).

Based on this knowledge and in view of the results shown in Table 2 above, the same bioinformatic procedure was carried out to identify a SMRV sequence hit and to study nucleotides substitution rate in this sequence hit.

Table 5 below summarizes the number of mapped sense and antisense reads obtained for each condition and the resulting coverage of the sequence.

TABLE 5 reads mapping, orientation and coverage.

|  | Number of reads | Coverage (%) |
|---|---|---|
| Condition 1 | | |
| Total | 1807960 | 100.00 |
| Sens | 1800981 | 100.00 |
| Antisens | 6979 | 45.48 |
| % of antisens reads | 0.386 | |
| Condition 2 | | |
| Total | 1601090 | 100.00 |
| Sens | 1594681 | 100.00 |
| Antisens | 6409 | 98.75 |
| % of antisens reads | 0.400 | |

TABLE 5-continued reads mapping, orientation and coverage.

|  | Number of reads | Coverage (%) |
| --- | --- | --- |
| Condition 3 | | |
| Total | 1816788 | 100.00 |
| Sens | 1808031 | 100.00 |
| Antisens | 8757 | 95.99 |
| % of antisens reads | | 0.482 |

The ratio of the "T-to-C" substitution rate calculated on the mismatches mapped on the SMRV reference genome in Condition 3 over the T-to-C substitution rate calculated on the mismatches mapped on the SMRV reference genome in Condition 1 is equal to 41.86:1 (Table 6).

This indicates an increase of the proportion of SMRV RNA species having incorporated 4sU, hence the neo-synthesis of viral RNA during the 9 hours incubation of the Vero cell culture in medium containing 4sU.

The method exemplified here allows thus the detection of replicating the (+)ssRNA-RT virus, SMRV, using metabolic labelling.

TABLE 6

T-to-C substitution rate.

|  | Condition 1 | Condition 2 | Condition 3 |
| --- | --- | --- | --- |
| Total mapped nt | 256422353 | 227104801 | 253753828 |
| Total mismatchs | 1288384 | 1132542 | 3531923 |
| Mismatch rate | 0.502% | 0.499% | 1.392% |
| Number of T→C substitutions | 54668 | 47393 | 2230483 |
| Number of T→C substitutions/ Total mismatchs | 4.243% | 4.185% | 63.152% |
| Number of T→C substitutions/ Total mapped nt | 0.021% | 0.021% | 0.879% |
| Other nt substitution rates/ Total mapped nt | | | |
| A→C | 0.08% | 0.08% | 0.07% |
| A→G | 0.03% | 0.03% | 0.04% |
| A→T | 0.02% | 0.02% | 0.02% |
| C→A | 0.10% | 0.10% | 0.09% |
| C→G | 0.03% | 0.03% | 0.03% |
| C→T | 0.02% | 0.02% | 0.04% |
| T→A | 0.05% | 0.05% | 0.06% |
| T→G | 0.05% | 0.05% | 0.07% |
| G→A | 0.06% | 0.06% | 0.07% |
| G→C | 0.03% | 0.02% | 0.03% |
| G→T | 0.02% | 0.02% | 0.02% |
| Minimum | 0.02% | 0.02% | 0.02% |
| Maximum | 0.10% | 0.10% | 0.09% |
| Average | 0.04% | 0.04% | 0.05% |

Example 3

Materials and Methods
Cells and Viruses

A vial of Vero cells (ATCC-CCL-81, batch #62488537, Molsheim, France) was frozen at passage 3 and then defrosted in a BSL-3 laboratory and the cells were grown in MEM supplemented with 10% FBS. Cells were used at passage 18.

A second vial of Vero cells (batch #70005907) was bought from the same source and used directly for PCR testing.

Tick-Borne Encephalitis Virus (TBEV) is a member of the family Flaviviridae, consisting of a ssRNA(+) genome. The Hypr strain (Wallner et al., 1996. *J Gen Virol*. 77(Pt 5):1035-42) was kindly supplied by Sarah Moutailler, ANSES, Maisons-Alfort, France).

TBEV Infection of Vero Cells

Vero cells were plated at 400,000 cells/well in 3 wells of a MW6 plate in order to reach $10^6$ cells/well after 24 hours. Cells were then infected with the Strain Hypr TBEV at a multiplicity of infection of 1, and incubated 1 hour on ice with agitation.

The medium was removed in one well just after incubation and the cells were lysed with 1 mL of Trizol and stored at −80° C. until RNA extraction (Condition "D0—no 4sU").

For the other two wells (Conditions 2, 3 and 4), the medium was removed and replaced by MEM+10% FBS and incubated overnight at 37° C.

4sU Labelling and RNA Extraction

Addition of 4-thiouridine (4sU) into the cell culture medium enables 4sU nucleotides to be incorporated into newly synthesized RNA. The reverse transcription of 4sU displays a certain percentage of misincorporation resulting in a T>C transition in the cDNA, which can be identified by sequencing (Herzog et al., 2017. *Nat Methods*. 14(12):1198-1204). The medium containing 800 µM 4sU was prepared by adding 8 µL of 100 nM 4sU in 992 µL of MEM. The day following viral infection, the medium was removed and replaced by either medium without 4sU in one well (Condition "D1—no 4sU") or 4sU-containing medium (800 µM) for the other well (Conditions "D1—with 4sU").

Six hours later, the medium was removed and replaced by fresh medium without 4sU in condition "D1—no 4sU", or by fresh 4sU-containing medium (800 µM) in condition "D1—with 4sU".

Three hours later, the medium was removed from the three wells and the cells were lysed with 1 mL of Trizol and stored at −80° C. until RNA extraction.

RNA extraction was performed in the dark using a chloroform:isoamyl alcohol mix 24:1 (Sigma Aldrich, Cat. No. 25666, Saint Louis, USA) followed by isopropanol/ethanol precipitation. During extraction, reducing agent was used to maintain the 4sU-treated sample under reducing conditions.

Alkylation was performed using the SLAMseq Kinetic kit—Anabolic Kinetics Module (Lexogen, Cat. No. 061, Vienna, Austria) for one part of the condition "D1—with 4sU" only. Total extracted RNA was mixed with iodoacetamide (IAA), which modifies the 4-thiol group of 4sU-containing nucleotides via the addition of a carboxyamidomethyl group leading to the condition "D1—with 4sU+ alkylation". This alkylation amplifies the frequency of T>C misincorporations during the reverse transcription. The other part was labelled "D1—with 4sU no alkylation".

The RNA was then purified using ethanol precipitation prior to proceeding to library preparation.

Library Preparation and Sequencing

The SMARTer Stranded Total RNA-Seq Kit—Pico Input Mammalian (ClonTech, Mountain View, USA) was used for a direct construction of libraries starting with 10 ng of RNA. The workflow used with this kit incorporates a proprietary technology (PathoQuest, Paris, France) that depletes ribosomal cDNA using probes specific to mammalian rRNA and some mitochondrial RNA. Sequencing was performed on the NextSeq instrument (Illumina, San Diego, United States) using the NextSeq 500/550 High Output kit v2 (FC-404-2002, Illumina). Sequencing was single-read with a read length of 150 nucleotides generating approximatively 125 million reads per sample.

Agnostic Bioinformatic Analysis

The raw data reads were filtered to select high-quality and relevant reads. Raw data was sorted to suppress or cut duplicates, low quality reads and homopolymers (PathoQuest proprietary software).

Sequences introduced during the preparation of Illumina libraries (adapters, primers) were removed with Skewer (Jiang et al., 2014. BMC Bioinformatics. 15:182).

Primate reads (from Vero cells) aligned to the human genome (Reference GRCh37/hg19) or reads aligned to bacterial rRNA were discarded. Local alignments were performed with BWA (Li et al., 2009. Bioinformatics. 25(14): 1754-60). Human genome was downloaded from the UCSC Genome Browser (Kent et al., 2002. Genome Res. 12(6): 996-1006). The bacterial rRNA database was initially downloaded from the EMBL-EBI ENA rRNA database (ebi.ac.uk/pub/databases/ena/rRNA/release) followed by an additional in-house sequence cleaning and clustering process. These filtered reads were considered as sequences of interest and were assembled into longer sequences named "contigs" with CLC assembly cell solution (Qiagen Hilden, Germany). Resulting contigs and non-assembled reads (singletons) were aligned using BLAST alignment (Altschul et al., 1990. J Mol Biol. 215(3):403-10) on viral and comprehensive databases. Contigs and singletons were first aligned on a viral nucleotide database. Hits with an e-value below $10^{-3}$ were aligned on a comprehensive nucleotide database. If the best hit was still a viral taxonomy, hits were reported.

Nucleotide viral and comprehensive databases were downloaded on November 2017 from the EMBL-EBI nucleotide sequence database STD. A proprietary software (PathoQuest, Paris, France) was developed to remove duplication and low confidence sequences (e.g., too short, multiple taxonomies, low-quality associated keywords). Contigs without any viral nucleotide hits were similarly aligned successively on viral and comprehensive protein databases to check for more distant viral hits. Protein viral and comprehensive databases were downloaded on November 2017 from the Uniref100 database (https://www.uniprot.org). While the Uniref100 database is already non-redundant, we utilized a taxonomic cleaning process to produce the final databases. The taxonomic assignment reported the best hit results with contigs not assigned after these two rounds of alignment being classified as unknown or non-viral species.

The above process identified a contig encompassing the full TBEV genome sequence (see "Results"). All the reads were then realigned with CLC assembly cell solution (Qiagen, Hilden, Germany) on this sequence to extract a final consensus sequence. The data retrieved from the condition "D0—no 4sU" allowed to identify contigs covering the whole genome of TBEV and SMRV and the resulting sequence was respectively labeled "TBEV REFERENCE" and "SMRV REFERENCE".

Estimation of T>C Substitution Ratio

In order to be able to detect viral sequences with a very high "T-to-C" substitution rate, each reference sequence was also modified by substituting every T by a C. These sequences were named "TBEV T-C REFERENCE" and "SMRV-T-C REFERENCE".

The "TBEV REFERENCE" and "TBEV T-C REFERENCE" and the "SMRV REFERENCE" and "SMRV T-C REFERENCE" were merged together to form two banks named "TBEV BLAST" and "SMRV BLAST". The set of quality filtered reads was then aligned by BLAST using these previously designed "BLAST" banks. The maximal e-value was set to $10^{-8}$. Only aligned reads were selected for the next step of the analysis.

The CLC program "cic_find_variations" was used to detect every mismatch at every position of the TBEV study reference. The global variations profile was then analyzed by a proprietary script (PathoQuest, Paris, France) to define each nucleotide substitution rate. The proportion of substituted nucleotides was compared to the total number of aligned nucleotides. For example, the "T-to-C" substitution rate was calculated using the following formula:

$$T \rightarrow C \text{ substitution rate} = \frac{\text{Number of } C \text{ nucleotides identified when a } T \text{ was expected}}{\text{Total number of expected } T}$$

The substitution rates for each time point were normalized with the following substitution index:

$$T \rightarrow C \text{ substitution index} = \frac{\text{``}T \rightarrow C\text{'' rate}}{\text{Mean (``}T \rightarrow A\text{'', ``}T \rightarrow G\text{'' rates)}}$$

As a quality control for the labelling, we checked the mean substitution index of a set of exons using non-labelled cells as a reference. Exons were used from the following human genes described by Eisenberg & Levanon (2013. Trends Genet. 29(10):569-74) (RefSeq accession number): C1orf43 (NM_015449), CHMP2A (NM_014453), EMC7 (NM_020154), GPI (NM_000175).

We used these human exons to identify their equivalent in the Cholorcebus sabeus genome, from whom the Vero cells are derived. The complete assembly of Chlorocebus sabeus (Accession number GCF_000409795.2) was retrieved from NCBI assembly database (https://www.ncbi.nlm nih.gov/assembly/). Selected human exons were mapped onto C.

*sabeus* assembly using minimap2 (Li, 2018. *Bioinformatics*. 34(18):3094-3100) and resulting .bam file was converted to .bed file using the bamtobed module from the BEDTools utility (Quinlan & Hall, 2010. *Bioinformatics*. 26(6):841-2). Only hits with mapping quality higher than 30 were retained (41 exons) and the corresponding sequences were extracted from *C. sabeus* assembly using the getfasta module from the BEDTools utility and indexed for further analyses. Labelling was considered satisfactory if the substitution index was superior to 10.

Stranded Analysis

A targeted and stranded analysis was performed on the identified TBEV reads. This analysis was based on a more stringent mapping alignment of filtered reads with the alignment providing a detailed horizontal genome coverage and depth profile. Local alignments were performed with BWA. Since the sample libraries were prepared using the SMARTer Stranded RNA-Seq Kit, the RNA strand information was also retained. As a result, a mapping alignment analysis was able to provide information on the mother strand of each read (sense or reverse relative to the mother strand).

Results

Identification of Adventitious Viruses by Agnostic RNA-Seq in Vero Cells

Vero cells were first put in contact with a high dose of TBEV at +4° C. (D0). At this temperature, only virus binding to cells receptors occurs and virus entry is blocked. Therefore, this experimental setting mimics the carryover of a non-replicating virus. RNAs were extracted and sequenced as a marker of DNA- or RNA virus infection. The results of the agnostic analysis and those of the mapping of the reads against the two main viral hits found by the agnostic analysis (TBEV and SMRV) are shown respectively in Table 7 and Table 8.

TABLE 7 number (% negative sense/total reads) of the reads onto TBEV and SMRV genomes and horizontal coverage of the genome (% genome). Reads were mapped on the genomes of TBV and SMRV found by the agnostic procedure (Table 8).

| Sample condition | D0 - no 4sU | D1 - no 4sU | D1 - with 4sU + alkylation | D1 - with 4sU no alkylation |
|---|---|---|---|---|
| TBEV reads | 160085 (0.27) | 6408291 (0.35) | 5240211 (0.36) | 5722338 (0.32) |
| TBEV horizontal coverage | 100 | 100 | 100 | 100 |
| SMRV reads | 1807960 (0.39) | 1601090 (0.40) | 1816788 (0.48) | 2479933 (0.37) |
| SMRV horizontal coverage | 100 | 100 | 100 | 100 |

TABLE 8

Agnostic analysis - Number of reads following each step o the filtering process, results of the de novo assembly and of the blast analysis.

| | D0 - no 4sU | D1 - no 4sU | D1 - with 4sU + alkylation | D1 - with 4sU no alkylation |
|---|---|---|---|---|
| Total reads | 153379022 | 153360490 | 149549706 | 163035957 |
| FILTERING | | | | |
| Duplicates/Quality | 84575371 | 85885045 | 73631007 | 82102171 |
| Adapters | 84575497 | 85884068 | 73629933 | 82101241 |
| Host | 19348675 | 21678833 | 27726895 | 21993690 |
| rRNA | 19314195 | 21637189 | 27664792 | 21957108 |
| ASSEMBLY | | | | |
| Contigs | 32777 | 246669 | 460995 | 337130 |
| Singletons | 2800174 | 2937361 | 3951554 | 2842044 |
| % assembled reads | 85.50% | 86.42% | 85.72% | 87.06% |
| TBEV RESULTS | | | | |
| Nb contigs | 4 | 127 | 143 | 104 |
| Nb reads in contigs | 100031 | 2514666 | 2255875 | 2060105 |
| Nb singletons | 145 | 5052 | 3932 | 3570 |
| Total reads | 100176 | 2519718 | 2259807 | 2063675 |
| Average contigs identity (%) | 91.23% | 92.06% | 91.71% | 90.53% |
| ADDITIONNAL CLOSE SPECIES (TOTAL READS) | | | | |
| Machupo mammarenavirus | 1 | 2 | | |
| Louping ill virus | | 14 | | |
| Bovine viral diarrhea virus 1 | 12 | 7 | 9 | 9 |
| Bovine viral diarrhea virus 2 | | 1 | | |
| Bovine viral diarrhea virus 3 | | 1 | | |
| Singapore grouper iridovirus | 48 | | 41 | 59 |
| Orthohepevirus A | | | | 1 |
| Rotavirus C | 1 | | | |
| Cercopithecine betaherpesvirus 5 | | 25 | | 2 |
| Stealth virus 4 | | | | 5 |
| Stealth virus 5 | | | 1 | |
| Human gammaherpescirus 8 | | 23 | 6 | |
| uncultured virus | | | 30 | |
| Simian retrovirus | | 3 | 17 | |
| Squirrel monkey retrovirus | 923291 | 837907 | 1064215 | 1107994 |
| Primate T-lymphotropic virus 1 | 5 | 29 | 10 | |
| Baboon endogenous virus | 8503 | 8691 | 7710 | 10617 |

TABLE 8-continued

Agnostic analysis - Number of reads following each step o the filtering process, results of the de novo assembly and of the blast analysis.

|  | D0 - no 4sU | D1 - no 4sU | D1 - with 4sU + alkylation | D1 - with 4sU no alkylation |
|---|---|---|---|---|
| Feline leukemia virus | 2 |  | 3 | 28 |
| Human endogenous retrovirus | 478 | 280 | 529 | 322 |
| Human endogenous retrovirus K | 16 | 35 | 37 | 37 |
| Human endogenous retrovirus W | 64 | 53 | 37 | 60 |
| Lnras* SN acutely transforming retrovirus |  |  |  | 9 |
| Retroviridae (no genus, no snecies) |  |  | 4 | 7 |

The main viral species detected at D0 was, as expected, TBEV, but also, unexpectedly, SMRV (Table 7). More than 160,000 TBEV reads out of a total of around 150 million raw reads (Table 8) were identified, covering the whole genome. Vero cells were then shifted at 37° C. to allow for virus entry and then incubated for one day before harvest. The number of reads strongly increased with between 5.2 million to 6.4 million TBEV reads recorded. Additionally, between 1.6 and 1.8 million reads mapping to SMRV-H (a SMRV isolated from a human lymphoid cell line (Oda et al., 1988. *Virology*. 167(2):468-76)) were also identified independent of the day of harvest. This meant that the SMRV transcripts were expressed by the cells without any relationship to experimental infection by TBEV.

We also identified a number of other hits (Table 8). The main additional hit was Baboon endogenous virus, a known endogenous virus of Vero cells (Ma et al., 2011. J Virol. 85(13):6579-88). A few hundred reads mapping to endogenous human retroviruses were also recorded. In our experience this finding is frequent in primate/human cell lines. We found also a few BVDV reads typically associated with the use of gamma-irradiated bovine serum. We also identified a few reads (<50) targeted to different herpes viruses which we considered as background noise.

Differentiation of Cell Infection Versus Carry-Over of Inert Sequences

Since our primary objective was to mimic challenging conditions for differentiation between cell infection from carryover while testing the capability of HTS for detecting early infection of cells, we compared results of cells put in contact with high doses of TBEV blocked for virus replication at +4° C. with those of cells infected with the same dose of virus 24 hours post-infection. The former mimicked cells inactivated virus or free nucleic acids and the latter mimicking cells infected just before banking. Since TBEV is a positive sense ssRNA virus, the negative sense RNA was used as a marker of virus replication. The three conditions tested at D1 (no 4uS; with 4sU+alkylation; with 4sU no alkylation) showed that 0.32 to 0.36% of the reads were negative sense compared to 0.27% at D0, a very small but highly significant difference (chi-square test, p<0.0001). This type of comparative analysis is not relevant for the chronic infection of cells by SMRV, a retrovirus for which transcription uses as matrix a DNA provirus and leads mainly to positive but also to negative sense RNAs (Manghera et al., 2017. *Virol J*. 14(1):9).

Figures 1A, 1B:
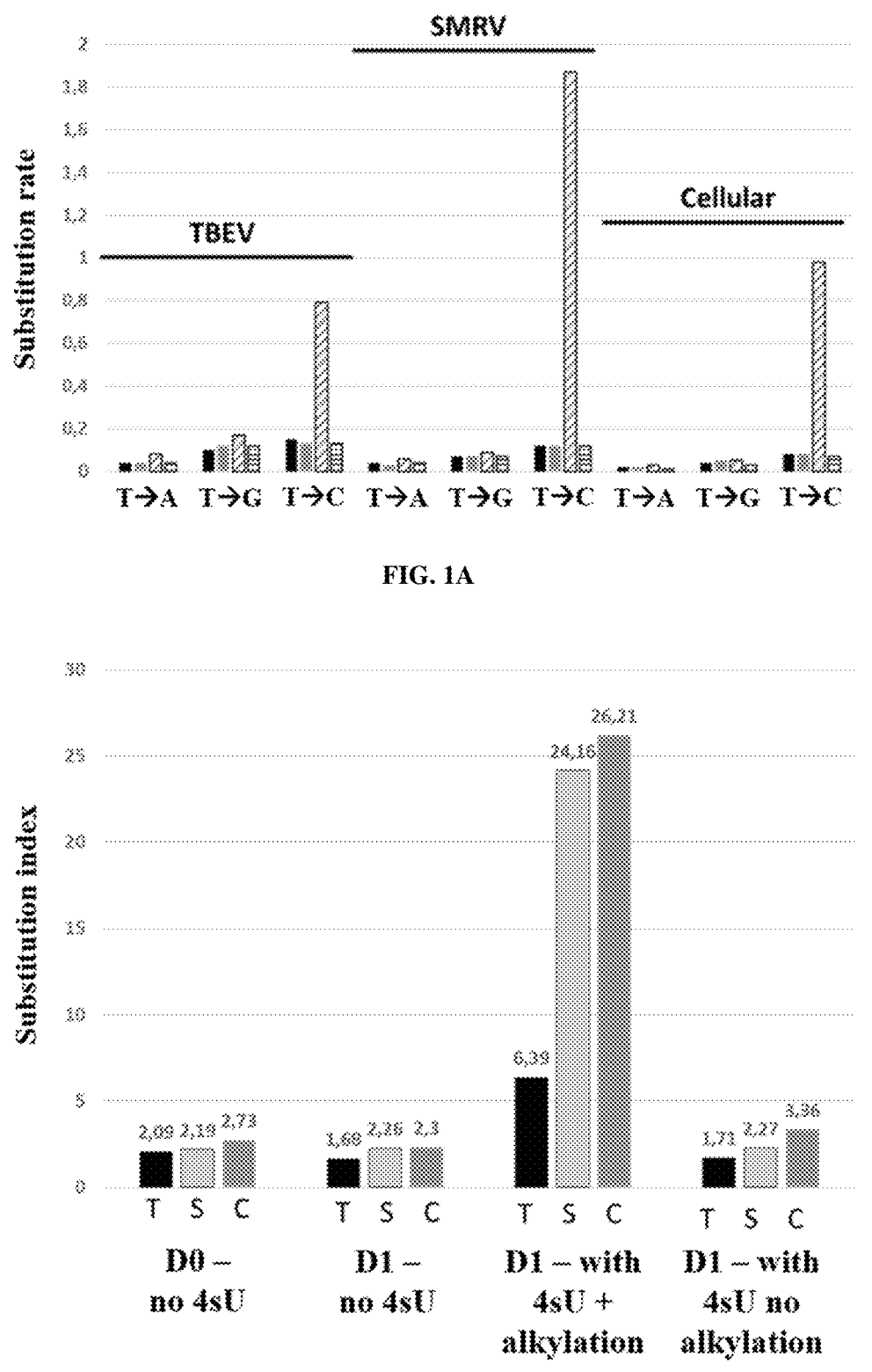

We then examined the TBEV rate of "T-to-C" substitution following metabolic labelling by 4sU of newly synthetized RNAs (Table 9 and FIG. 1).

TABLE 9 substitution rate of T nucleotides and substitution index

| Sample condition | D0 - no 4sU | D1 - no 4sU | D1 - with 4sU + alkylation | D1 - with 4sU no alkylation |
|---|---|---|---|---|
| --- TBEV --- | | | | |
| Rate "T-to-C" (%) | 0.15 | 0.13 | 0.79 | 0.13 |
| Rate "T-to-A" (%) | 0.04 | 0.04 | 0.08 | 0.04 |
| Rate "T-to-G" (%) | 0.10 | 0.12 | 0.17 | 0.12 |
| Substitution index | 2.09 | 1.68 | 6.39 | 1.71 |
| --- SMRV --- | | | | |
| Rate "T-to-C" (%) | 0.12 | 0.12 | 1.87 | 0.12 |
| Rate "T-to-A" (%) | 0.04 | 0.03 | 0.06 | 0.04 |
| Rate "T-to-G" (%) | 0.07 | 0.07 | 0.09 | 0.07 |
| Substitution index | 2.19 | 2.26 | 24.16 | 2.27 |
| --- Cellular transcripts --- | | | | |
| Rate "T-to-C" (%) | 0.08 | 0.08 | 0.98 | 0.07 |
| Rate "T-to-A" (%) | 0.02 | 0.02 | 0.03 | 0.01 |
| Rate "T-to-G" (%) | 0.04 | 0.05 | 0.05 | 0.03 |
| Substitution index | 2.73 | 2.30 | 26.21 | 3.36 |

At D1, in absence of metabolic labelling, the ratio of "T-to-C" was very low (0.13%) and similar to those of "T-to-A" or "T-to-G" (0.04-0.13%) resulting in a calculated background substitution index of 1.68. Similar results were obtained at D0 indicating good reproducibility of the background of substitution.

In clear contrast, the "T-to-C" substitution rate for labelled and alkyled RNAs of TBEV at D1 was much higher (0.79%) resulting in a substitution index of 6.4, a 3.8-fold increase compared to the background. The substitution index at D1 for the labelled and alkyled SMRV cells was 24.16, 10.7-fold over background.

Comparisons between metabolically labelled and non-labelled RNAs would necessitate two conditions of culture. As a result, we also compared the TBEV and SMRV substitution indexes obtained at D1 for the 4sU-labelled culture, with and without RNA alkylation. This necessitates only one condition of culture, followed by RNA extraction and alkylation, or no treatment. The low level of substitutions in RNA 4sU-labeled, non-alkylated cells did not impair the detection by blast analysis of potential viral hits (Table 8). As shown in Table 9 and FIG. 1B the substitution index of the 4sU-labelled, non-alkylated RNAs remained low and close to that of the non-labelled condition (1.71 and 2.27 for TBEV and SMRV, respectively, increasing to 4.0 and 10.6-fold respectively in the alkylated condition). This suggests that non-alkylated RNAs extracted from the same cell culture can be used to establish the reference consensus viral bank used to calculate substitution rates. Therefore, our results show that following 4sU labelling of cells, RNA-Seq was able to specifically identify newly synthetized viral RNAs with a high signal-to-background noise ratio.

Figure 3:
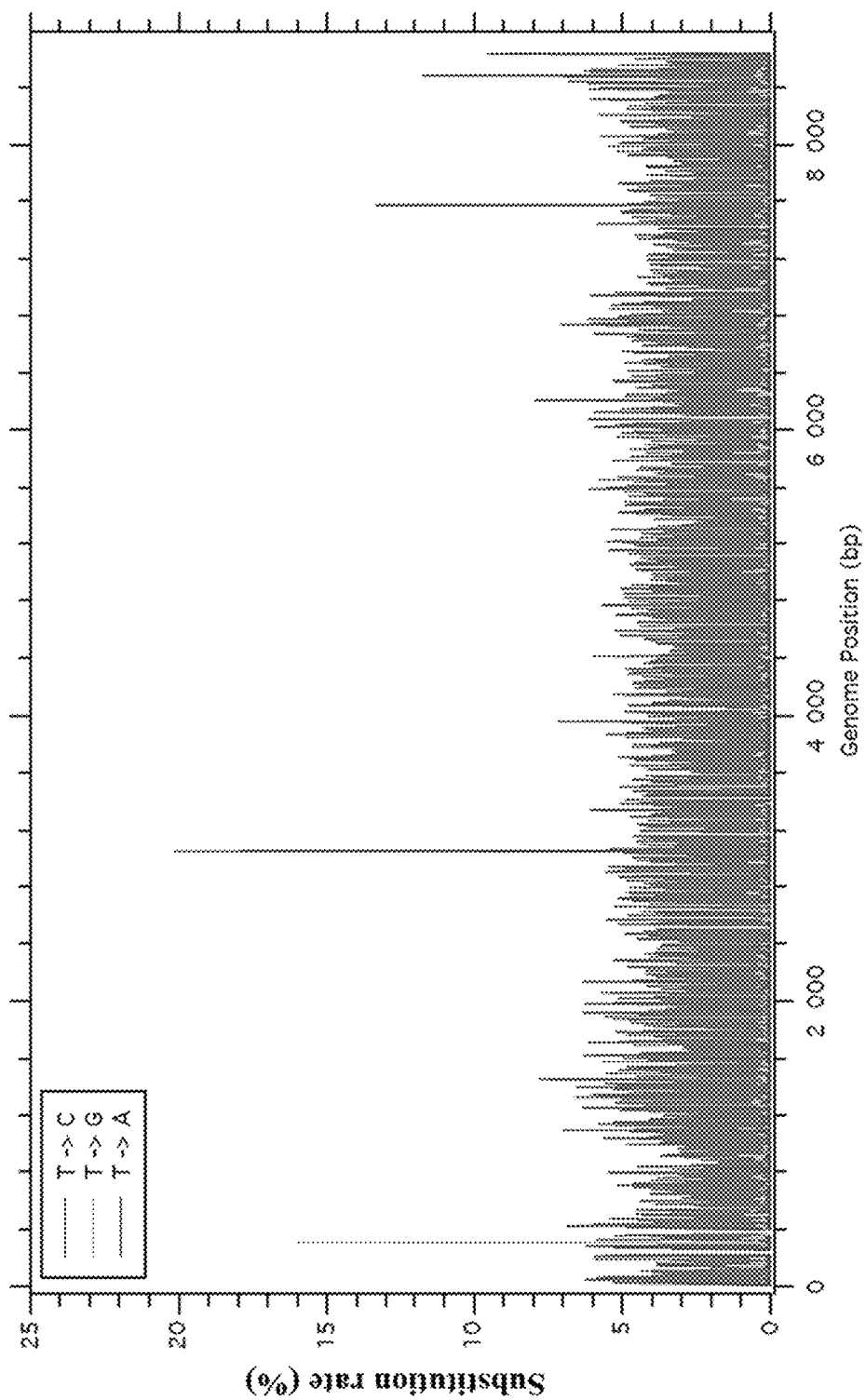
FIG. 3 is a graph illustrating the substitution rates (in %) of T nucleotides to C, G or A, in a sample treated with 4sU and alkylated, using as microbial nucleic acid sequence hit a SMRV consensus sequence built from data of the current condition.

Finally, we also compared the ratio between the T→C substitution rate in 4sU-labelled, alkylated cells and the average T→A and T→G substitutions observed in the same cells, for TBEV (FIG. 2) and SMRV (FIG. 3).

These ratios are given in Table 10. A ratio of substitution above 1 is indicative of active transcription in the sample. These results therefore clearly show that the method of the invention is able to discriminate and detect live TBEV and SMRV by comparing the substitutions rates of different nucleotides in a single condition (D1—with 4sU+alkylation).

TABLE 10 ratios of T→C substitution vs average T→A/T→G substitutions

| | TBEV | SMRV |
|---|---|---|
| T→A | 0.10 | 0.10 |
| T→C | 0.83 | 3.54 |
| T→G | 0.18 | 0.12 |
| T→C/Avg(T→A, T→G) | 5.87 | 32.41 |

Example 4

Materials and Methods

Cells and Mollicutes

A549 (ATCC_CCL-185) cells were grown in DMEM-Dulbecco's Modified Eagle Medium to circa 70% confluence in a 6 well plate before contamination.

*Acholeplasma Laidlawii* is the Representative of the Mollicute Family Selected to Infect the A549 Cells.

*Acholeplasma laidlawii* Infection of A549 Cells

At circa 70% confluence, the culture medium of the A549 cells was changed to MEM-Earle medium supplemented with 7% fetal bovine serum and 1% L-glutamine without antibiotics. Cells were infected at various infectious doses of *Acholeplasma laidlawii* at day 0 (Table 11). At day 5, 4-thiouridine (4sU) (800 µM) was added to the culture medium 9 hours, 6 hours and 3 hours before supernatant harvest. 2 mL of culture medium were removed after 5 days of incubation at 37° C. and clarified by centrifugation at 200 g for 5 minutes. 1 mL of clarified supernatant centrifuged at 15 000-20 000 g during 10 minutes and 900 µL of supernatant were removed and the pellet was homogenized in the 100 µL remaining supernatant. Samples were then frozen prior to nucleic acids extraction.

Addition of 4-thiouridine (4sU) into the cell culture medium enables 4sU nucleotides to be incorporated into newly synthesized RNA. The reverse transcription of 4sU displays a certain percentage of misincorporation resulting in a T>C transition in the cDNA, which can be identified by sequencing (Herzog et al., 2017. *Nat Methods*. 14(12):1198-1204).

TABLE 11 description of the test items

| Test items | *Acholeplasma* sp. infection dose (cfu/mL) | Viable *Acholeplasma* sp. count at day 5 (cfu/mL) |
|---|---|---|
| CTRL5Tag | none | none |
| LC5 | 5 | >$10^9$ |
| LC5Tag* | 5 | >$10^9$ |

TABLE 11-continued description of the test items

| Test items | *Acholeplasma* sp. infection dose (cfu/mL) | Viable *Acholeplasma* sp. count at day 5 (cfu/mL) |
|---|---|---|
| Diluted LC5Tag* | | ~2.5 × $10^7$ |
| HC__HK5tag | 2.5 × $10^7$** | none |
| 4° HC__HK5tag | 2.5 × $10^7$** | none |
| HC__G5tag | 2.5 × $10^7$ | $10^4$ |

*This test item will be evaluated in this study with and without dilution; the sample LC5Tag will be diluted to obtain the similar counts of *acholeplasma* sp prior to inactivation and infection of the cells.
**Prior to inactivation.
CTRL5Tag is a control sample, not infected with *Acholeplasma laidlawii* and labelled with 4SU at day 5.
LC5 is a sample infected with a Low Concentration of *Acholeplasma laidlawii* at day 5.
LC5Tag is a sample infected with a Low Concentration of *Acholeplasma laidlawii* and 4 SU labelled at day 5.
HC__HK5tag is a sample infected with a High Concentration of *Acholeplasma laidlawii* heat killed before infection and 4 SU labelled at day 5.
HC__G5tag is a sample infected with a high dose of *Acholeplasma laidlawii* treated with gentamycin before infection and 4 SU labelled at day 5.

RNA Extraction

RNA extraction was performed in the dark using a chloroform:isoamyl alcohol mix 24:1 (Sigma Aldrich, Cat. No. 25666, Saint Louis, USA) followed by isopropanol/ethanol precipitation. During extraction, reducing agent was used to maintain the 4sU-treated sample under reducing conditions.

Alkylation was performed using the SLAMseq Kinetic kit—Anabolic Kinetics Module (Lexogen, Cat. No. 061, Vienna, Austria) for one part of the condition "D1—with 4sU" only. Total extracted RNA was mixed with iodoacetamide (IAA), which modifies the 4-thiol group of 4sU-containing nucleotides via the addition of a carboxyamidomethyl group leading to the condition "D1—with 4sU+alkylation". This alkylation amplifies the frequency of T>C misincorporations during the reverse transcription. The other part was labelled "D1—with 4sU no alkylation".

The RNA was then purified using ethanol precipitation prior to proceeding to library preparation.

Library Preparation and Sequencing

The SMARTer Stranded Total RNA-Seq Kit—Pico Input Mammalian (ClonTech, Mountain View, USA) was used for a direct construction of libraries starting with 10 ng of RNA. The depletion of ribosomal RNA of bacterial origin (16S and 23S) is performed on total RNA using the Ribominus Bacteria Transcriptome analysis kit (thermoFisher). Depletion of ribosomal cDNA using probes specific to mammalian rRNA and some mitochondrial RNA is also performed (included in the SMARTer Stranded Total RNA-Seq kit, prior to the library preparation using the manufacturer's recommendation (ClonTech). Sequencing was performed on the Next Seq instrument (Illumina, San Diego, United States) using the NextSeq mid output flow cell (FC-404-1001, Illumina). Sequencing was single-read with a read length of 150 nucleotides generating approximatively 125 million reads per sample.

Agnostic Bioinformatic Analysis

The raw data reads were filtered to select high-quality and relevant reads. Raw data was sorted to suppress or cut duplicates, low quality reads and homopolymers (PathoQuest proprietary software).

Sequences introduced during the preparation of Illumina libraries (adapters, primers) were removed with Skewer (Jiang et al., 2014. *BMC Bioinformatics*. 15:182).

Filtered reads of the LC5 condition were considered first as sequences of interest. As this condition very likely includes a high content of unlabeled sequences of the organism of interest, this will allow the reconstruction of the genome of the targeted organism (*Acholeplasama laidlawii*). LC5 reads were therefore assembled into longer sequences named "contigs" with Megahit (Li et al., 2015. *Bioinformatics*. 31(10):1674-1676). Resulting contigs were then mapped back with minimap2 (Li, 2018. *Bioinformatics*. 34(18):3094-3100) onto *Acholeplasma laidlawii* strain PG8A genome (RefSeq AccNum CP000896.1). Positive hits were then tiled on the *Acholeplasma laidlawii* strain PG8A genome using Mummer 3 (Kurtz et al., 2004. *Genome Biol.* 5(2):R12) in order to:

1. confirm the identity of contigs potentially detected as *A. laidlawii*,
2. ensure completeness of the newly build sequence.

Once the identity of the contigs has been assessed and the tiling validated, contigs were pooled in a .fasta file to serve as reference genome (hereafter called LC5_ALAID_CNS) for further analyses.

Estimation of T>C Substitution Ratio

In order to detect *A. laidlawii* sequences with a very high number of T→C substitutions, the set of quality filtered reads was mapped back to LC5_ALAID_CNS with minimap2 in non-multimap mode (Li, 2018. *Bioinformatics*. 34(18):3094-3100). The pileup module of the htsbox software (https://github.com/lh3/htsbox) was then used to detect all mismatches (with a base quality at least equal to 30) at every position of the LC5_ALAID_CNS sequence. The global variations profiles were then analyzed using a proprietary script (PathoQuest, Paris, France) to define each nucleotide substitution rates. The proportion of substituted nucleotides was compared to the total number of aligned nucleotides. For example, the T→C substitution rate was calculated using the following formula:

$$T \to C \text{ substitution rate} = \frac{\text{Number of } C \text{ nucleotides identified when a } T \text{ was expected}}{\text{Total number of expected } T}$$

The substitution rates for each time point were normalized with the following substitution index:

$$T \to C \text{ substitution index} = \frac{\text{``}T \to C\text{'' rate}}{\text{Mean (``}T \to A\text{'', ``}T \to G\text{'' rates)}}$$

Results

Sequencing Throughput

Sequencing runs throughput are reported in Table 12. For almost all conditions, more than 10 million of single end reads have been produced. For each condition, more than 90% of reads have been retained after the filtering step, indicating that the sequencing runs were of good quality and thus suitable for subsequent analyses.

TABLE 12

Sequencing throughput for all experimental condition

| Test items | Raw Reads | Filtered Reads | Ratio |
|---|---|---|---|
| CTRL5Tag | 14,092,086 | 12,698,272 | 0.90 |
| LC5 | 14,922,171 | 14,766,414 | 0.99 |
| LC5Tag* | 17,690,706 | 17,519,522 | 0.99 |
| Diluted LC5Tag* | 17,124,090 | 16,894,486 | 0.99 |

TABLE 12-continued

Sequencing throughput for all experimental condition

| Test items | Raw Reads | Filtered Reads | Ratio |
|---|---|---|---|
| HC_HK5tag | 20,410,793 | 20,076,010 | 0.98 |
| 4° HC_HK5tag | 20,410,793 | 20,076,010 | 0.98 |
| HC_G5tag | 16,591,955 | 16,060,004 | 0.97 |

Reference Genome Reconstruction

LC5 reads assembly process allowed the generation of a set of 877 contigs (cumulative length 1,374,213; Min_length=201; Avg_length=1,566.9; Max_length=15,043). Remapping onto *A. laidlawii* PG8A (CP000896.1) genome sequence allowed the unambiguous selection of 662 contigs (cumulative length 1,287,020; Min_length=301; Avg_length=1,944.1; Max_length=15,043) as candidates for LC5_ALAID_CNS reconstruction. As a first check, GC content distribution and statistics were investigated to evidence a possible mix of organisms in contigs set (FIG. 4).

Figure 4:
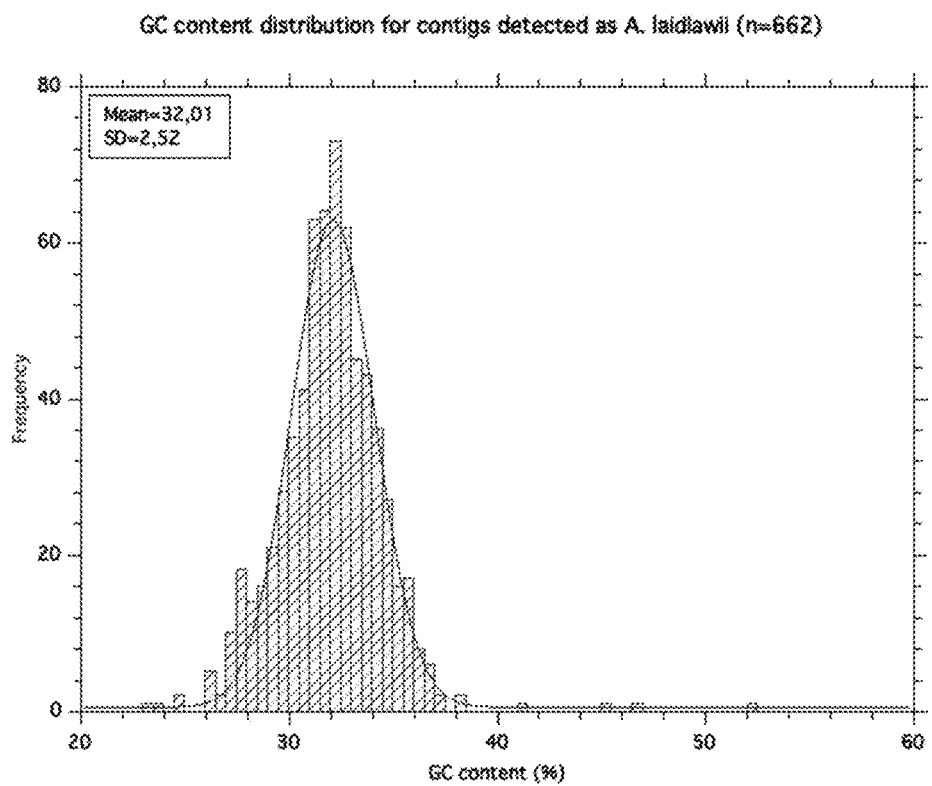
FIG. 4 is a graph showing the GC content distribution of the 662 contigs selected as candidates for LC5_ALAID_CNS reference genome reconstruction.

As seen in FIG. 4, the GC content distribution is unimodal suggesting a low probability of the presence of contigs representative of several organisms in the contigs set. Furthermore, the mean GC content of this set is not significantly different from the expectation (32.01% vs 31.93% for *A. laidlawii* str. PG8A).

To ensure that we were able to reconstruct the entire genome (or at least a significant portion) of a close relative of *A. laidlawii* str. PG8A, we "tiled" the latter with the selected contigs from the initial assembly of reads of the LC5 experimental condition. The results are presented in FIG. 5.

Figure 5:
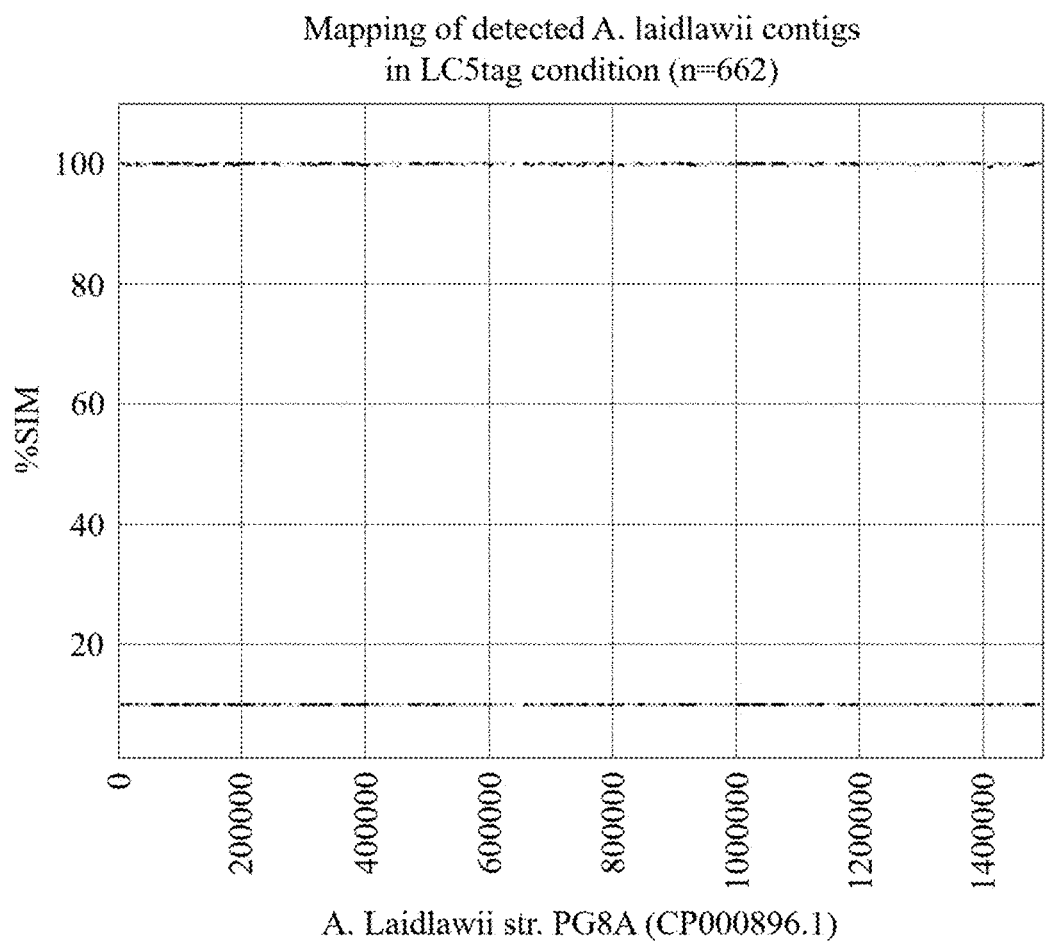
FIG. 5 is a graph showing the tiling of the A. laidlawii str. PG8A genome with the 662 selected contigs from the initial assembly of reads of the LC5 experimental condition. Matching contigs (forward in black, reverse in grey) are reported at their real percentage of similarity (upper part) and normalized at 10% similarity to flatten the coverage and ease visualization.

As shown in FIG. 5, the 662 contigs set covers almost entirely the *A. laidlawii* str. PG8A with high similarity (higher than 99% in all cases; data not shown) which strongly suggests that the reconstructed LC5_ALAID_CNS is a very close relative of *A. laidlawii* str. PG8A.

In conclusion, we were able to:
1. select a clean set of contigs corresponding to *A. laidlawii*, and
2. cover the complete genome of a close relative (*A. laidlawii* str. PG8A).

This process thus validates our reference sequence LC5_ALAID_CNS for further analyses.

Substitution Rates and Indexes

Lowly covered positions might induce biases in rate estimates as they account with the same weight as pretty well covered ones. Indeed, if a position is covered only 3 times and is once a T→C substitution, the T→C substitution rate at this position would be 33% regardless of the fact that it might be either a true substitution or a sequencing/assembly error. Therefore, to avoid overestimates of substitution rates and therefore substitution indexes, we conducted the analysis first selecting all detected events (i.e., covered at least once (1×)) and then selecting events at least covered 20 times (i.e., 20×), the latter being considered as highly confident events.

Substitution rates and indexes are reported in Table 13. Overall, we show here that transition T→C rate are always higher than transversion T→A and T→G rates, which is expected as classical mutation patterns favor transitions upon transversions.

Moreover, the T→C substitution rates are significantly higher for LC5tag and 40-fold diluted LC5tag conditions compared to all other conditions (including the high load inactivated sample (HC_HK5Tag)), whatever the selection level of events. Moreover, the inclusion of lowly covered position in this analysis had little impact on the results since observed rates were not significantly different at 1× and 20× thresholds, still the latter would limit the background noise. The same trend is observable for substitution indexes.

TABLE 13

Substitution rates and substitution index (SI) for each experimental condition for all detected events (1X threshold) and for highly confident events (20X Threshold).

|  | 1x threshold | | | | 20x threshold | | | |
| --- | --- | --- | --- | --- | --- | --- | --- | --- |
|  | Substitution rate | | | Substitution | Substitution rate | | | Substitution |
|  | T > A | T > C | T > G | index | T > A | T > C | T > G | index |
| LC5 | 0.02 | 0.07 | 0.04 | 2.03 | 0.02 | 0.07 | 0.04 | 2.03 |
| LC5tag | 0.04 | 1.02 | 0.06 | 20.59 | 0.04 | 0.90 | 0.06 | 17.71 |
| LC5tag Dilution 40X | 0.04 | 1.36 | 0.05 | 29.94 | 0.04 | 1.27 | 0.05 | 27.90 |
| HC_HK5tag | 0.05 | 0.13 | 0.06 | 2.32 | 0.05 | 0.13 | 0.07 | 2.31 |
| 4° C. HC_HK5tag | 0.04 | 0.11 | 0.06 | 2.11 | 0.04 | 0.11 | 0.07 | 2.11 |
| HC_G5tag | 0.04 | 0.15 | 0.05 | 3.24 | 0.04 | 0.15 | 0.05 | 3.26 |
| CTRL5tag | 0.12 | 1.41 | 0.89 | 2.77 | 0.13 | 1.42 | 0.90 | 2.76 |

In conclusion, the reported results showed that experiments expected to be spiked by *A. laidlawii* and 4sU-labeled were detected as such.

Positional Analysis

We have reported a global increase in substitution rates and substitution indexes. In order to investigate whether these increases result from substitution hotspots, we conducted a positional analysis evaluating substitution rates along the LC5_ALAID_CNS reference sequence (FIGS. 6A-G).

Figure 6A:
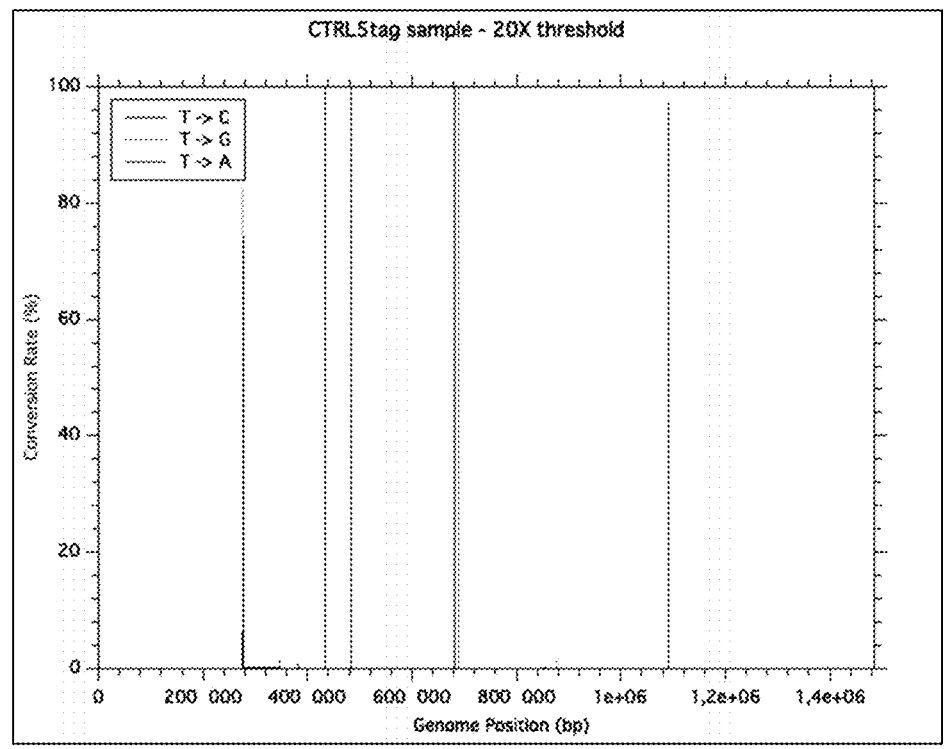
FIGS. 6A to 6G are seven graphs illustrating the substitution rates (or conversion rate) (in %) of T nucleotides to C, G or A along the LC5_ALAID_CNS reference sequence for the different tested conditions. Only high confident events (≥20× depth) have been selected for the analysis. 6A: CTRL5tag condition; 6B: LC5 condition; 6C: LC5tag condition; 6D: 40fold diluted LC5tag condition; 6E: HC_HK5tag condition; 6F: HC_HK5tag condition; 6G: HC_G5tag condition

We noticed the presence of *A. laidlawii* reads in the CTRL5tag experimental condition as some peaks were visible though this condition has not been spiked with *Acholeplasma laidlawii* (FIG. 6A). Most of the rates reached 100% suggesting that those substitutions are actually real SNPs. This observation suggested either a contamination at experimental level or a cross index contamination during the sequencing phase when multiplexing samples (the so-called index hopping). Nevertheless, as it concerned a quite limited number of positions, it did not impair the analysis.

Figure 6B:
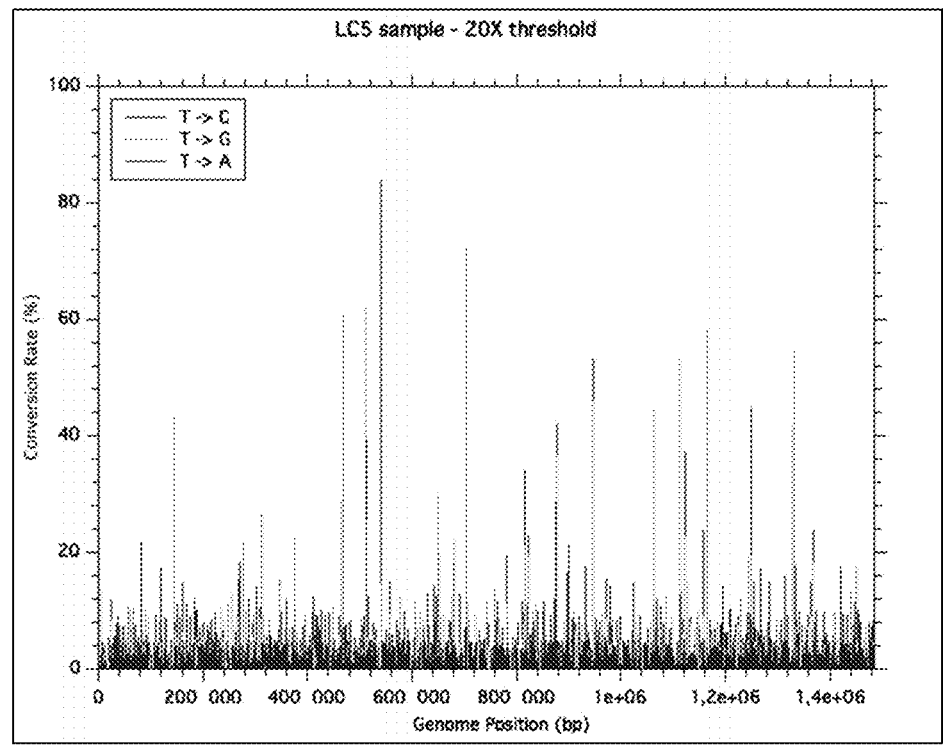
Figure 6C:
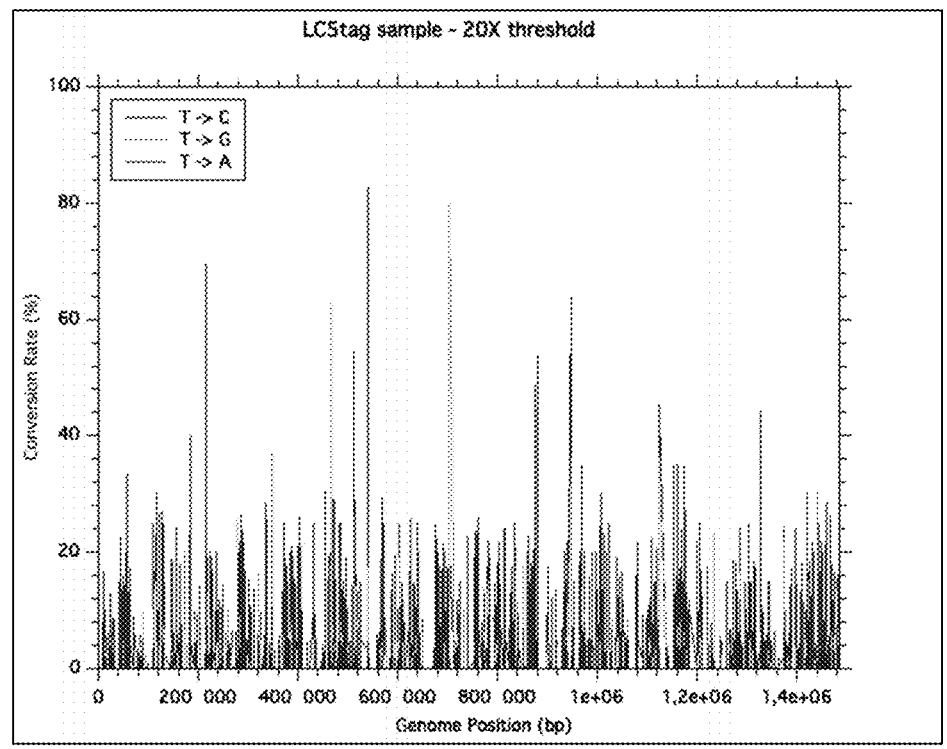
Figure 6D:
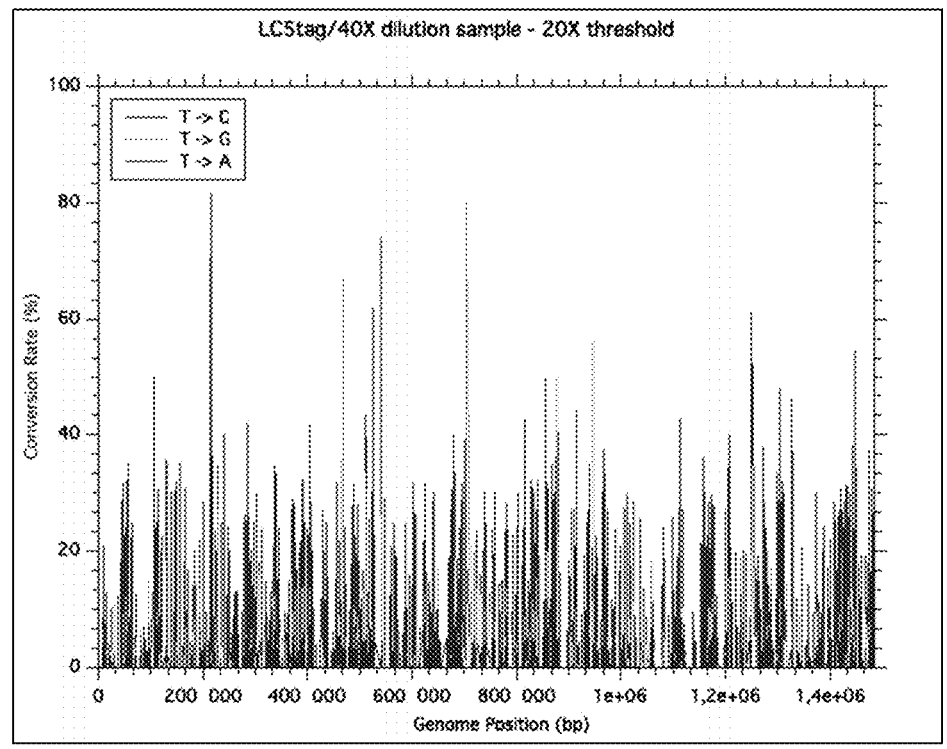

FIG. 6B shows a rather low background of substitutions for LC5 condition with all the genome positions well-covered (i.e., no coverage hole). No real dominant substitution type is visible, which is in agreement with the global scale analysis. In contrast, for LC5tag and 40fold diluted LC5tag conditions, one could distinguish large T→C peaks emerging from the background, indicating a successful labelling and thus active transcription in *A. laidlawii* (FIGS. 6C and 6D).

Figure 6E:
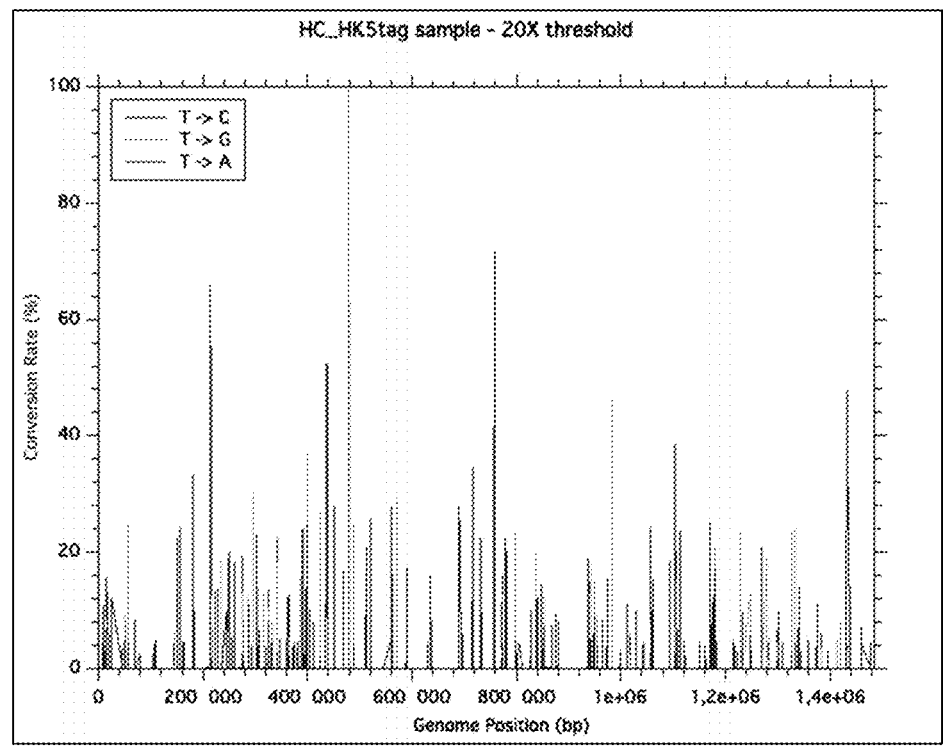
Figure 6F:
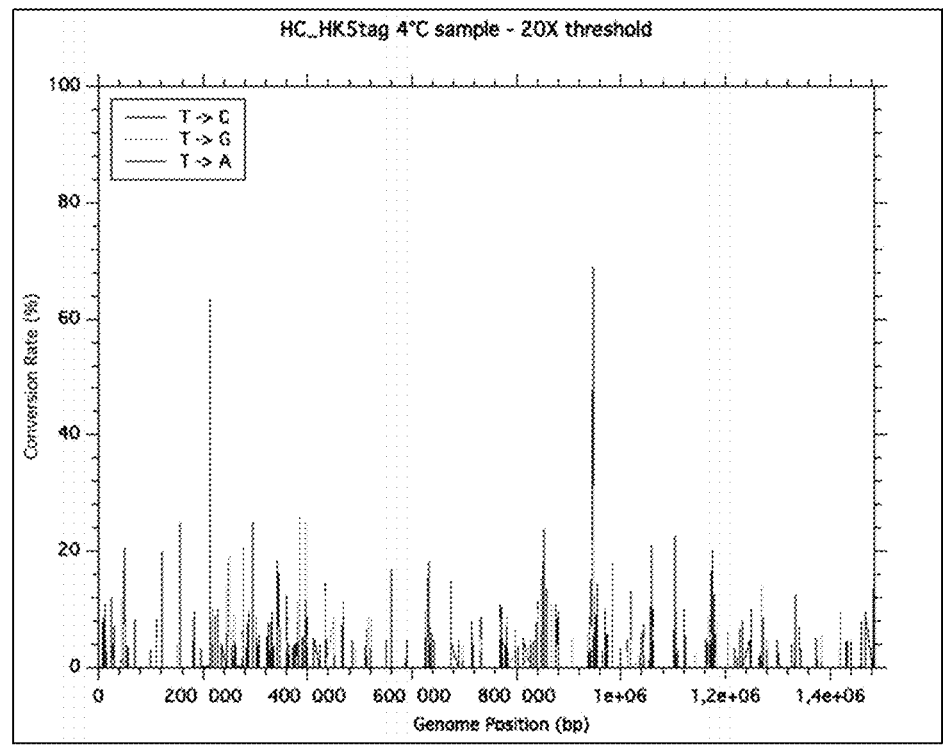

FIGS. 6E and 6F show the results of the 4sU-labelling of experimental conditions where *A. laidlawii* cells have been killed by heat (HC_HK5tag and 4° HC_HK5tag). In both cases, we observed a smaller number of peaks (and especially T→C peaks) compared to LC5tag and 40X_LC5tag condition, confirming the lower amount of extracted RNA due to a low remaining number of living bacterial cells in the medium after heating.

Figure 6G:
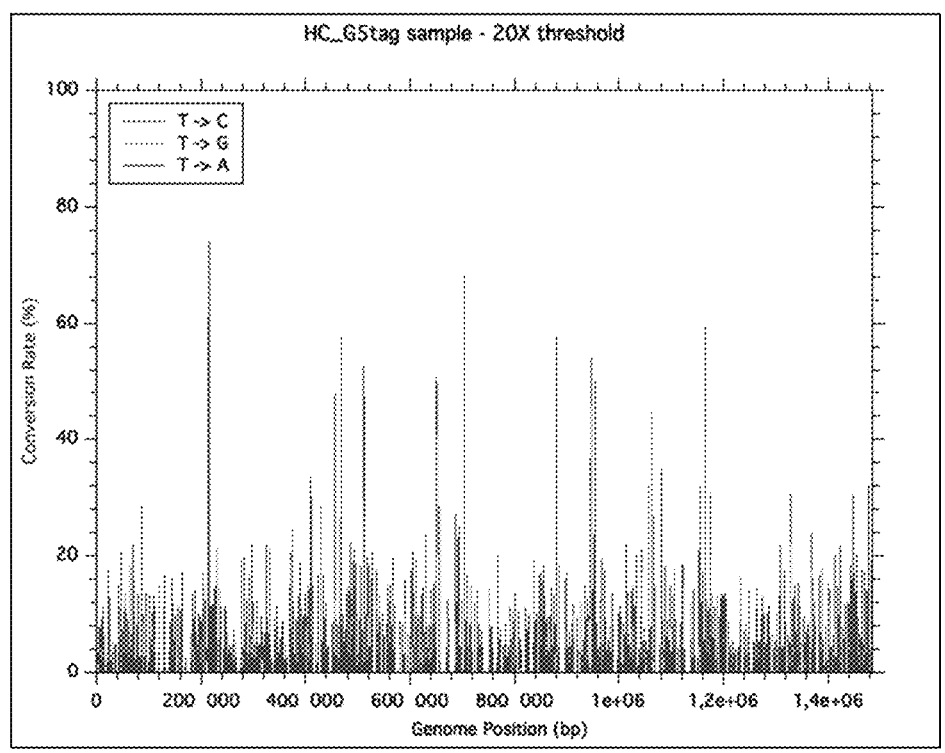

Likewise, the gentamycin treatment had the same effect (HC_G5 condition; FIG. 6G), but was apparently much moderate compared to the effect of heat in HC_HK5tag experimental conditions (FIGS. 6E and 6F). Yet, the 4sU-labelling was still visible and confirm the global analyses with a moderate substitution index (Table 13).

Example 5

Materials and Methods

Cells and Mollicutes

A549 (ATCC_CCL-185) cells are grown in DMEM-Dulbecco's Modified Eagle Medium to circa 70% confluence in a 6 well plate before contamination.

*Acholeplasma* Sp or *Mycoplasma* sp Infection of A549 Cells

At circa 70% confluence, the culture medium of the A549 cells is changed to MEM-Earle medium supplemented with 7% fetal bovine serum and 1% L-glutamine without antibiotics. Cells will be infected at various infectious doses of *Acholeplasma* sp or *Mycoplasma* sp.

Several conditions are tested, among which:
CTRL5Tag: control sample, not infected with *Acholeplasma* sp or *Mycoplasma* sp and labelled with 4-SU at day 5;
LC5: sample infected with a Low Concentration of *Acholeplasma* sp or *Mycoplasma* sp;
LC5Tag: sample infected with a Low Concentration of *Acholeplasma* sp or *Mycoplasma* sp and 4-SU labelled at day 5;
HC_HK5tag: sample infected with a High Concentration of *Acholeplasma* sp or *Mycoplasma* sp heat killed before infection and 4-SU labelled at day 5;
HC_G5tag: sample infected with a high dose of *Acholeplasma* sp or *Mycoplasma* sp treated with gentamycin before infection and 4-SU-labelled at day 5.

At day 5, 4-thiouridine (4sU) (800 μM) is added to the culture medium 9 hours, 6 hours and 3 hours before cell harvest. Culture medium is removed after 5 days of incubation at 37° C., cells are pelleted and frozen prior to RNA extraction.

Addition of 4-thiouridine (4sU) into the cell culture medium enables 4sU nucleotides to be incorporated into newly synthesized RNA. The reverse transcription of 4sU displays a certain percentage of misincorporation resulting in a T>C transition in the cDNA, which can be identified by sequencing (Herzog et al., 2017. *Nat Methods.* 14(12):1198-1204).

RNA Extraction

RNA extraction is performed in the dark using a chloroform:isoamyl alcohol mix 24:1 (Sigma Aldrich, Cat. No. 25666, Saint Louis, USA) followed by isopropanol/ethanol precipitation. During extraction, reducing agent is used to maintain the 4sU-treated sample under reducing conditions.

Alkylation is performed using the SLAMseq Kinetic kit—Anabolic Kinetics Module (Lexogen, Cat. No. 061, Vienna, Austria) for one part of the condition "D1—with 4sU" only. Total extracted RNA is mixed with iodoacetamide (IAA), which modifies the 4-thiol group of 4sU-containing nucleotides via the addition of a carboxyamidomethyl group leading to the condition "D1—with 4sU+ alkylation". This alkylation increases the frequency of T>C misincorporations during the reverse transcription.

The RNA is then purified using ethanol precipitation prior to proceeding to library preparation.

Library Preparation and Sequencing

The SMARTer Stranded Total RNA-Seq Kit—Pico Input Mammalian (ClonTech, Mountain View, USA) is used for a direct construction of libraries starting with 10 ng of RNA. The depletion of ribosomal RNA of bacterial origin (16S and 23S) is performed on total RNA using the Ribominus Bacteria Transcriptome analysis kit (ThermoFisher). Depletion of ribosomal cDNA using probes specific to mammalian rRNA and some mitochondrial RNA is also performed (included in the SMARTer Stranded Total RNA-Seq kit, prior to the library preparation using the manufacturer's recommendations (ClonTech)). Sequencing is performed on the Illumina instrument (Illumina, San Diego, United States) using the NextSeq 500/550 High Output kit v2 (FC-404-2002, Illumina). Sequencing is paired-end with a read length of 150 nucleotides generating approximatively 100 million reads per sample.

Agnostic Bioinformatic Analysis

The raw data reads are filtered to select high-quality and relevant reads. Raw data are sorted to suppress or cut duplicates, low quality reads and homopolymers (PathoQuest proprietary software).

Sequences introduced during the preparation of Illumina libraries (adapters, primers) are removed with Skewer (Jiang et al., 2014. *BMC Bioinformatics*. 15:182).

Filtered reads of the negative control conditions (unlabeled, inactivated or both) are considered first as sequences of interest. As these conditions very likely include a high load of sequences of the organism of interest, this allows the reconstruction of the genome of the targeted organism (*Acholeplasma* sp or *Mycoplasma* sp). These reads are therefore assembled into longer sequences named "contigs" with Megahit (Li et al., 2015. *Bioinformatics*. 31(10):1674-1676). Resulting contigs are then mapped back with minimap2 (Li, 2018. *Bioinformatics*. 34(18):3094-3100) onto *Acholeplasma* sp or *Mycoplasma* sp strain PG8A genome (RefSeq AccNum CP000896.1). Positive hits are then tiled on the *Acholeplasma* sp or *Mycoplasma* sp strain PG8A genome using Mummer 3 (Kurtz et al., 2004. *Genome Biol.* 5(2):R12) in order to:
1. confirm the identity of contigs potentially detected as *Acholeplasma* sp or *Mycoplasma* sp, and
2. ensure completeness of the newly build sequence (hereafter referred as ALAID_CNS).

Estimation of T>C Substitution Ratio

In order to detect *Acholeplasma* sp or *Mycoplasma* sp sequences with a very high number of T→C substitutions, the set of quality filtered reads is mapped back to ALAID_CNS with minimap2 in non-multimap mode (Li, 2018. *Bioinformatics*. 34(18):3094-3100). The pileup module of the htsbox software (https://github.com/lh3/htsbox) is then used to detect all mismatches (with a base quality at least equal to 30) at every position of the ALAID_CNS sequence. The global variations profiles are then analyzed using a proprietary script (PathoQuest, Paris, France) to define each nucleotide substitution rates. The proportion of substituted nucleotides is compared to the total number of aligned nucleotides. For example, the T→C substitution rate is calculated using the following formula:

$$T \to C \text{ substitution rate} = \frac{\text{Number of } C \text{ nucleotides identified when a } T \text{ was expected}}{\text{Total number of expected } T}$$

The substitution rates for each time point is normalized with the following substitution index:

$$T \to C \text{ substitution index} = \frac{\text{"}T \to C\text{" rate}}{\text{Mean ("}T \to A\text{", "}T \to G\text{" rates)}}$$

The invention claimed is:

1. A method for discriminating between live and dead microbes in a sample, comprising discriminating between transcriptionally-active and inert microbial nucleic acid sequences in the sample, wherein the method comprises the steps of:
   (a) sequencing a set of RNAs extracted from the sample, wherein the set of RNAs is obtained by culturing the sample in the presence of an RNA-labelling agent and further by submitting the extracted RNAs to conditions promoting thymidine (T)-to-cytidine (C) substitutions; thereby obtaining a set of sequence reads;
   (b) determining a consensus microbial nucleic acid sequence through:
      (i) aligning the set of sequence reads or contigs onto a database comprising microbial nucleic acid sequences, and
      (ii) deriving a consensus microbial nucleic acid sequence assembled de novo from said sequence reads that have mapped with an expected value (e-value) below $10^{-2}$ to a microbial nucleic acid sequence of the database;
   (c) determining the number and/or rate of substituted nucleotides in the set of sequence reads that have mapped with an e-value below $10^{-2}$ to a microbial nucleic acid sequence of the database at step (b) in comparison with the consensus microbial nucleic acid sequence assembled de novo at step (b); and
   (d) concluding that the consensus microbial nucleic acid sequence belongs to a live microbe if, of the set of sequence reads that have mapped with an e-value below $10^{-2}$ to a microbial nucleic acid sequence of the database at step (b), the number and/or rate of T-to-C substitutions determined in step (c) is greater than the average number and/or rate of substitutions of all other nucleotides in the same sequence reads,
wherein steps (c) and (d) do not require the use of an external microbial nucleic acid sequence reference.

2. The method according to claim 1, wherein step (d) comprises concluding that the consensus nucleic acid sequence assembled de novo belongs to a live microbe if, of the sequence reads that have mapped with an e-value below $10^{-2}$ to a microbial nucleic acid sequence of the database at step (b), the number and/or rate of T-to-C substitutions determined at step (c) is greater than the average number and/or rate of T-to-adenine (A) and T-to-guanosine (G) substitutions in the same sequence reads.

3. The method according to claim 1, wherein the RNA-labelling agent is a thiol-labelled RNA precursor.

4. The method according to claim 3, wherein the thiol-labelled RNA precursor is selected from the group consisting of 4-thiouridine, 2-thiouridine, 2,4-dithiouridine, 2-thio-4-deoxyuridine, 5-carbethoxy-2-thiouridine, 5-carboxy-2-thiouridine, 5-(n-propyl)-2-thiouridine, 6-methyl-2-thiouridine and 6-(n-propyl)-2-thiouridine, thereby obtaining thiouridine-labelled RNAs.

5. The method according to claim 3, wherein the thiol-labelled RNA precursor is 4-thiouridine.

6. The method according to claim 1, wherein conditions promoting T-to-C substitutions comprise chemically modifying the RNAs; and further reverse-transcribing said chemically-modified RNAs.

7. The method according to claim 1, wherein conditions promoting T-to-C substitutions comprise chemically modifying the RNAs by alkylation, oxidative-nucleophilic-aromatic substitution or osmium-mediated transformation; and further reverse-transcribing said chemically-modified RNAs.

8. The method according to claim 1, wherein conditions promoting T-to-C substitutions comprise chemically modifying the RNAs by alkylation; and further reverse-transcribing said chemically-modified RNAs.

9. The method according to claim 1, wherein conditions promoting T-to-C substitutions comprise alkylation using an alkylating agent selected from the group consisting of iodoacetamide, iodoacetic acid, N-ethylmaleimide and 4-vinylpyridine.

10. The method according to claim 1, wherein conditions promoting T-to-C substitutions comprise alkylation using iodoacetamide.

11. The method according to claim 1, wherein the step of sequencing the set of RNAs comprises:
(i) reverse-transcribing RNAs, thereby obtaining a cDNA library,
(ii) optionally, amplifying said cDNA library, and
(iii) sequencing said cDNA library.

12. The method according to claim 11, wherein, during reverse-transcription at step (i), labelled RNAs undergo a first-strand synthesis with A-to-G substitutions and a second-strand synthesis leading to T-to-C substitutions in the cDNA library when the sample was cultured in the presence of an RNA-labelling agent and that the labelled RNAs are submitted to conditions promoting T-to-C substitutions.

13. The method according to claim 11, wherein sequencing said cDNA library at step (iii) is performed by Next-Generation Sequencing (NGS), deep sequencing or targeted sequencing of custom sequences.

14. The method according to claim 1, wherein the microbe is selected from the group consisting of viruses, bacteria, archaea, fungi and protozoans.

15. A method of treating a subject affected with a microbial infection, comprising:
(a) providing a sample from said subject,
(b) performing the method according to claim 1 on said sample,
(c) diagnosing the subject as having a microbial infection if the consensus microbial nucleic acid sequence assembled de novo belongs to a live microbe, and
(d) treating the subject if said subject was diagnosed as having a microbial infection in step (c).

16. The method of treating according to claim 15, wherein step (d) comprises administering to said subject at least one antiviral, antibacterial, antifungal or antiprotozoal agent.

17. A method for assessing the risk of microbial contamination in a non-biological sample, comprising:
(a) providing a non-biological sample,
(b) performing the method according to claim 1 on said non-biological sample, and
(c) concluding that the non-biological sample is at risk of being contaminated if the consensus microbial nucleic acid sequence assembled de novo belongs to a live microbe.

18. The method for assessing the risk of microbial contamination according to claim 17, wherein the non-biological sample is selected from the group consisting of an environmental sample, a food sample and a preservation medium.

19. The method according to claim 1, wherein the e-value with which the sequence reads have mapped to a microbial nucleic acid sequence of the database at step (b) is below $10^{-3}$.

20. The method according to claim 1, wherein step (b) further comprises:
assembling the sequence reads into contigs, and the consensus microbial nucleic acid sequence is determined through:
aligning the contigs assembled from the sequence reads onto a database comprising microbial nucleic acid sequences, and
deriving the consensus microbial nucleic acid sequence assembled de novo from said contigs that have mapped with an e-value below $10^{-2}$ to a microbial nucleic acid sequence of the database.

21. The method according to claim 1, wherein step (b) further comprises:
filtering the set of sequence reads before aligning the sequence reads onto a database comprising microbial nucleic acid sequences, and
deriving the consensus microbial nucleic acid sequence assembled de novo from said sequence reads that have mapped with an e-value below $10^{-2}$ to a microbial nucleic acid sequence of the database.

22. The method according to claim 21, wherein filtering the set of sequence reads comprises one or several of: suppressing sequence read duplicates, suppressing low quality sequence reads, suppressing sequence read homopolymers, removing adapters and/or indexes used for sequencing, discarding endogenous sequence reads, and discarding unwanted sequence reads.

* * * * *